United States Patent
Hiraoka

(10) Patent No.: US 9,380,996 B2
(45) Date of Patent: Jul. 5, 2016

(54) ULTRASOUND ENDOSCOPE

(71) Applicant: OLYMPUS CORPORATION, Tokyo (JP)

(72) Inventor: Jin Hiraoka, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/630,755

(22) Filed: Feb. 25, 2015

(65) Prior Publication Data

US 2015/0173711 A1 Jun. 25, 2015

Related U.S. Application Data

(63) Continuation of application No. PCT/JP2013/073986, filed on Sep. 5, 2013.

(60) Provisional application No. 61/696,920, filed on Sep. 5, 2012.

(51) Int. Cl.
*A61B 8/12* (2006.01)
*A61B 8/00* (2006.01)
(Continued)

(52) U.S. Cl.
CPC .............. *A61B 8/445* (2013.01); *A61B 1/0005* (2013.01); *A61B 1/00087* (2013.01); *A61B 1/00098* (2013.01); *A61B 1/00133* (2013.01); *A61B 1/00177* (2013.01); *A61B 1/018* (2013.01);
(Continued)

(58) Field of Classification Search
CPC .... A61B 5/005; A61B 5/100098; A61B 5/05; A61B 17/22; A61B 17/28; A61B 1/05; A61B 8/08; A61B 8/01; A61B 8/125
See application file for complete search history.

(56) References Cited

U.S. PATENT DOCUMENTS 6,338,717 B1 1/2002 Ouchi
6,390,973 B1 5/2002 Ouchi
(Continued)

FOREIGN PATENT DOCUMENTS

| DE | 199 29 314 A1 | 12/1999 |
|----|---|---|
| EP | 2 138 092 A1 | 12/2009 |
| JP | H05-344973 A | 12/1993 |

(Continued)

OTHER PUBLICATIONS

International Search Report dated Oct. 1, 2013 issued in PCT/JP2013/073986.
(Continued)

*Primary Examiner* — Joel Lamprecht
(74) *Attorney, Agent, or Firm* — Scully, Scott, Murphy & Presser, P.C.

(57) ABSTRACT

An ultrasound endoscope includes an insertion portion, an ultrasound transducer provided at a distal end portion of the insertion portion, a first opening portion provided at a distal end portion of the insertion portion, a second opening portion and a raising stand provided at the distal end portion of the insertion portion. Furthermore, the raising stand includes a first contact portion that comes into contact with a treatment instrument protruding from the first opening portion for causing the treatment instrument to extend in a first direction and a second contact portion that comes into contact with a treatment instrument protruding from the second opening portion for causing the treatment instrument to extend in a second direction different from the first direction.

7 Claims, 16 Drawing Sheets

(51) Int. Cl.
*A61B 1/00* (2006.01)
*A61B 1/018* (2006.01)

(52) U.S. Cl.
CPC .................. *A61B 8/12* (2013.01); *A61B 8/4483* (2013.01); *A61B 8/4494* (2013.01)

(56) References Cited

U.S. PATENT DOCUMENTS

2011/0065986 A1 3/2011 Geitz et al.
2012/0078041 A1 3/2012 Kitano et al.

FOREIGN PATENT DOCUMENTS

| JP | H11-276489 A | 10/1999 |
|---|---|---|
| JP | 2006-020725 A | 1/2006 |
| JP | 2006-246933 A | 9/2006 |
| JP | 2008-029384 A | 2/2008 |
| JP | 2008-043616 A | 2/2008 |
| JP | 4896275 B2 | 3/2012 |

OTHER PUBLICATIONS

Extended Supplementary European Search Report dated Mar. 22, 2016 in European Application No. 13 83 6060.7.

ULTRASOUND ENDOSCOPE

CROSS REFERENCE TO RELATED APPLICATION

This application is a continuation application of PCT/JP2013/073986 filed on Sep. 5, 2013 and claims benefit of U.S. Provisional Patent Application No. 61/696,920 filed in the U.S.A. on Sep. 5, 2012, the entire contents of which are incorporated herein by this reference.

BACKGROUND OF THE INVENTION

1. Field of the Invention

The present invention relates to an ultrasound endoscope, and relates to an ultrasound endoscope capable of performing both endoscopic ultrasound-guided fine needle aspiration (EUS-FNA) and endoscopic retrograde cholangiopancreatography (ERCP).

2. Description of the Related Art

Conventionally, endoscopes are widely used for various inspections and treatments inside a subject.

In recent years, ultrasound endoscopes that allow endoscopic ultrasound-guided fine needle aspiration (EUS-FNA) to be performed by inserting a needle from a digestive tract for pathological examination using ultrasound images and extracting cells, or endoscopes for performing endoscopic retrograde cholangiopancreatography (ERCP) that inserts a fine tube into a pancreatic duct or bile duct, injects a contrast medium and examines a change in the pancreatic duct or bile duct while checking the tube position by radiography are being developed and commercialized.

In the case of the ultrasound endoscope used for endoscopic ultrasound-guided fine needle aspiration (hereinafter referred to as "EUS-FNA"), since a raising angle of a treatment instrument protruding from a distal end portion of an insertion portion is less than 90 degrees with respect to an insertion axis direction of the insertion portion, it is difficult for an operator to perform endoscopic retrograde cholangiopancreatography (hereinafter referred to as "ERCP") using an EUS-FNA ultrasound endoscope. For this reason, for example, when the operator inserts an EUS-FNA-enabled ultrasound endoscope into the stomach and observes the pancreas or the like while watching at the ultrasound image, if a lesioned part is discovered in the pancreas or the like from the ultrasound image and endoscopic retrograde cholangiopancreatography (ERCP) needs to be performed, the operator pulls out the ultrasound endoscope from the subject, and inserts an ERCP endoscope into the subject to perform ERCP. That is, the ultrasound endoscope is switched over to the ERCP endoscope.

In the ERCP endoscope, the raising angle of a treatment instrument is, for example, 90 degrees or more. This is because when inserting the treatment instrument such as cannula into the duodenal papilla in ERCP, the treatment instrument needs to protrude from the distal end portion of the insertion portion at an angle of 90 degrees or more with respect to the axial direction of the insertion portion.

During operation, the operation of switching the ultrasound endoscope over to the ERCP endoscope is complicated and also time-consuming. Therefore, to enable one ultrasound endoscope to perform treatments of both EUS-FNA and ERCP, an ultrasound endoscope may be considered which has a structure that allows the raising angle of the treatment instrument to be increased. However, since a puncture needle used during EUS-FNA is rigid, if the operator considerably bends the puncture needle beyond a certain limit, the needle itself may be broken or a bending tendency may be formed on the needle making it impossible to pull out the needle, and it is thereby not possible to increase the raising angle of the treatment instrument of the ultrasound endoscope.

Thus, as disclosed in U.S. Patent Publication No. 6338717, an ultrasound endoscope is proposed which includes a channel that allows both an EUS-FNA treatment instrument and an ERCP treatment instrument to be inserted thereinto and two raising stands for raising the respective treatment instruments.

SUMMARY OF THE INVENTION

An ultrasound endoscope according to an aspect of the present invention includes: an insertion portion configured to extend in a longitudinal direction and be inserted into a living body; an ultrasound transducer provided at a distal end portion of the insertion portion and emitting ultrasound sideward at a predetermined angle with respect to an insertion axis of the insertion portion; a first opening portion provided at the distal end portion of the insertion portion; a second opening portion provided at the distal end portion of the insertion portion at a position upper side than the first opening portion; a raising stand provided at the distal end portion of the insertion portion and movable between a first position proximate to the first opening portion and the second opening portion and a second position away from the first opening portion and the second opening portion; a first contact portion provided along the raising stand from a proximal end portion to a distal end portion and that comes into contact with a side face of a first treatment instrument protruding from the first opening portion to cause the first treatment instrument to extend in a first direction; and a second contact portion provided on the distal end portion of the raising stand and that comes into contact with a side face of a second treatment instrument protruding from the second opening portion to cause the second treatment instrument to extend in a second direction different from the first direction.

DETAILED DESCRIPTION OF THE PREFERRED EMBODIMENT

Hereinafter, embodiments of the present invention will be described with reference to the accompanying drawings.
(First Embodiment)
(Configuration of Ultrasound Endoscope System)

Figure 1:
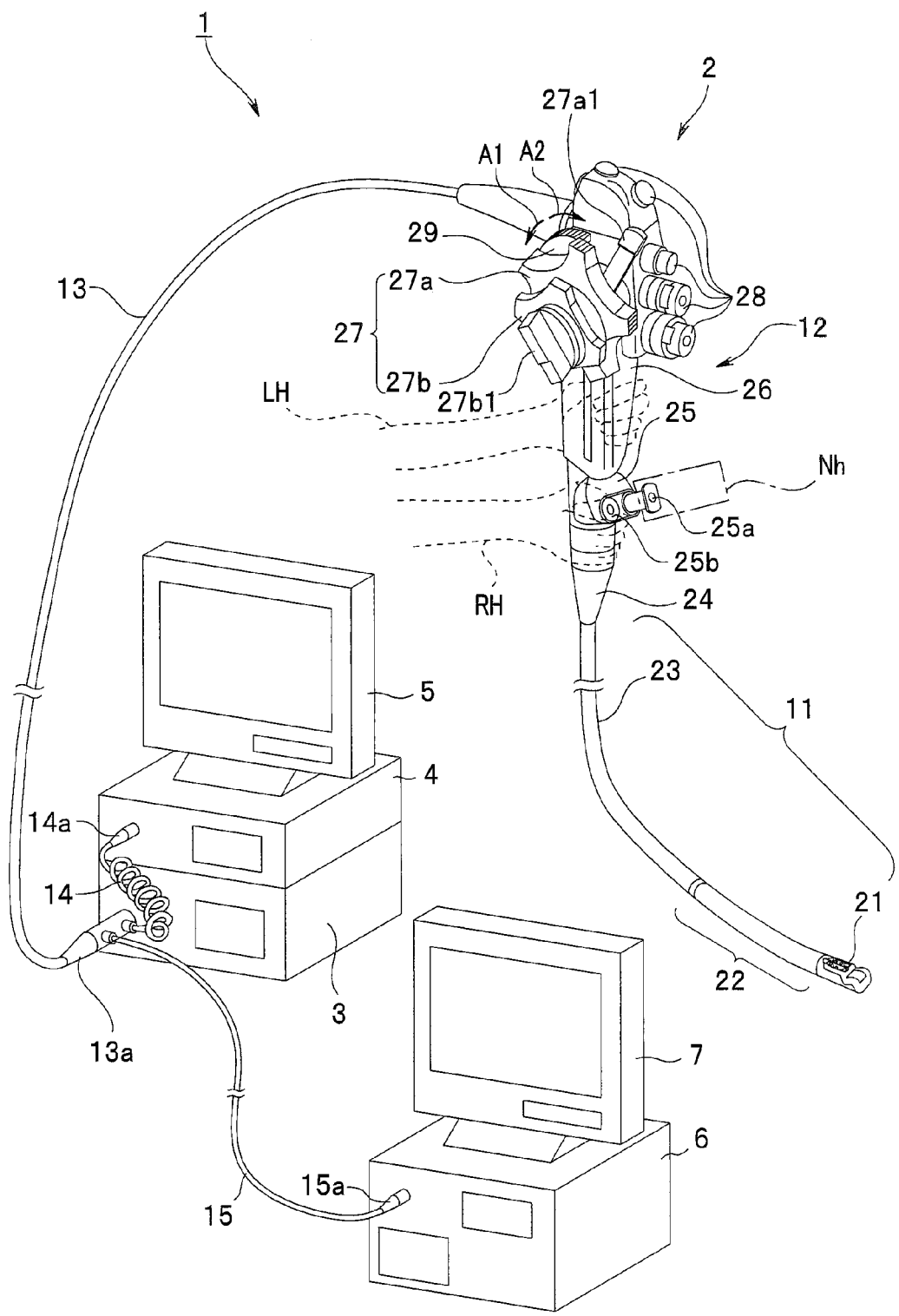
FIG. 1 is a configuration diagram illustrating an overall ultrasound endoscope system according to a first embodiment of the present invention.

FIG. 1 is a configuration diagram illustrating an overall ultrasound endoscope system of the present embodiment.

An ultrasound endoscope system 1 is configured by including an ultrasound endoscope (hereinafter simply referred to as "endoscope") 2, a light source apparatus 3, a video processor 4, a monitor 5 for displaying an optical image, an ultrasound observation apparatus 6 and a monitor 7 for displaying an ultrasound image.

The endoscope 2 includes an insertion portion 11, an operation portion 12 from which this insertion portion 11 extends and a universal cord 13 that extends from the operation portion 12. The insertion portion 11 extends in a longitudinal direction and configured to be inserted into a living body. The universal cord 13 is connected to the light source apparatus 3 via a scope connector 13a provided at a proximal end portion. A coiled scope cable 14 and an ultrasound signal cable 15 extend from this scope connector 13a. An electric connector portion 14a is provided at one end of the scope cable 14 and this electric connector portion 14a is connected to the video processor 4. An ultrasound connector portion 15a is provided at one end of the ultrasound signal cable 15 and this ultrasound connector portion 15a is connected to the ultrasound observation apparatus 6.

The insertion portion 11 is configured by consecutively connecting a distal end portion 21, a bending portion 22 and a flexible tube portion 23 in that order from the distal end. Two channel opening portions, an optical observation window, an optical illuminating window and an ultrasound transducer, which will be described later, or the like are arranged on one side of the distal end portion 21.

The operation portion 12 is configured by including a bend preventing portion 24 from which the insertion portion 11 extends, a channel opening setting portion 25, an operation portion body 26 making up a grip portion, a bending operation portion 27 including two bending operation knobs 27a and 27b provided so as to superimpose on one another on one upper side of this operation portion body 26, a plurality of switches 28 that instruct the execution of various endoscope functions and a raising lever 29 for operating a raising stand which will be described later.

The channel opening setting portion 25 is provided on one side in the lower part of the operation portion body 26 and provided with two forceps ports 25a and 25b. The respective forceps ports 25a and 25b disposed at the channel opening setting portion 25 of the operation portion 12 communicate with two channel opening portions provided at the distal end portion 21 of the insertion portion 11 via two treatment instrument channels (not shown) provided in the insertion portion 11. The forceps port 25a is a channel opening for endoscopic ultrasound-guided fine needle aspiration (FNA) and the forceps port 25b is a channel opening for endoscopic retrograde cholangiopancreatography (ERCP). A puncture needle handle portion Nh shown by a single-dot dashed line is fitted into the forceps port 25a.

The two forceps ports 25a and 25b are arranged at the channel opening setting portion 25 such that when the operator brings the right hand RH close to the channel opening setting portion 25, the forceps port closer to the right hand RH becomes the forceps port 25b and the forceps port farther from the right hand RH becomes the forceps port 25a.

More specifically, as shown by a dotted line in FIG. 1, the operator manipulates the treatment instrument inserted into each forceps port by the right hand RH while holding the operation portion body 26 by the left hand LH. The manipulation using the treatment instrument such as ERCP cannula has a higher degree of difficulty than manipulation using a treatment instrument of an EUS-FNA puncture apparatus.

Thus, the forceps port 25b for a treatment instrument such as cannula requiring fine manipulation when the operator holds the operation portion body 26 by the left hand LH is arranged at the channel opening setting portion 25 so as to be located on the right side compared to the forceps port 25a when seen from the operator.

The bending knob 27a is a vertical direction bending knob and the bending knob 27b is a horizontal direction bending knob. A bending fixing lever 27a1 for fixing the vertical direction bending state is provided on the proximal end side of the bending knob 27a and a bending fixing lever 27b1 for fixing the horizontal direction bending state is provided on the distal end side of the bending knob 27b.

Examples of the plurality of switches 28 include an air/water feeding button, a suction button and a freeze button.

An image pickup section for acquiring an optical image inside a subject, an illumination section and an ultrasound transducer section for acquiring an ultrasound tomographic image inside the subject are provided at the distal end portion 21 of the endoscope 2. This allows the operator to insert the endoscope 2 into the subject and causes the monitors 5 and 7 to display an optical image and an ultrasound tomographic image inside the subject at a desired position in the subject respectively.

The endoscope 2 of the present embodiment is an endoscope capable of performing both endoscopic ultrasound-guided fine needle aspiration (FNA) and endoscopic retrograde cholangiopancreatography (ERCP) as a single unit.
(Configuration of Distal End Portion)

Hereinafter, a configuration of the distal end portion 21 of the insertion portion 11 of the endoscope 2 will be described.

Figure 2:
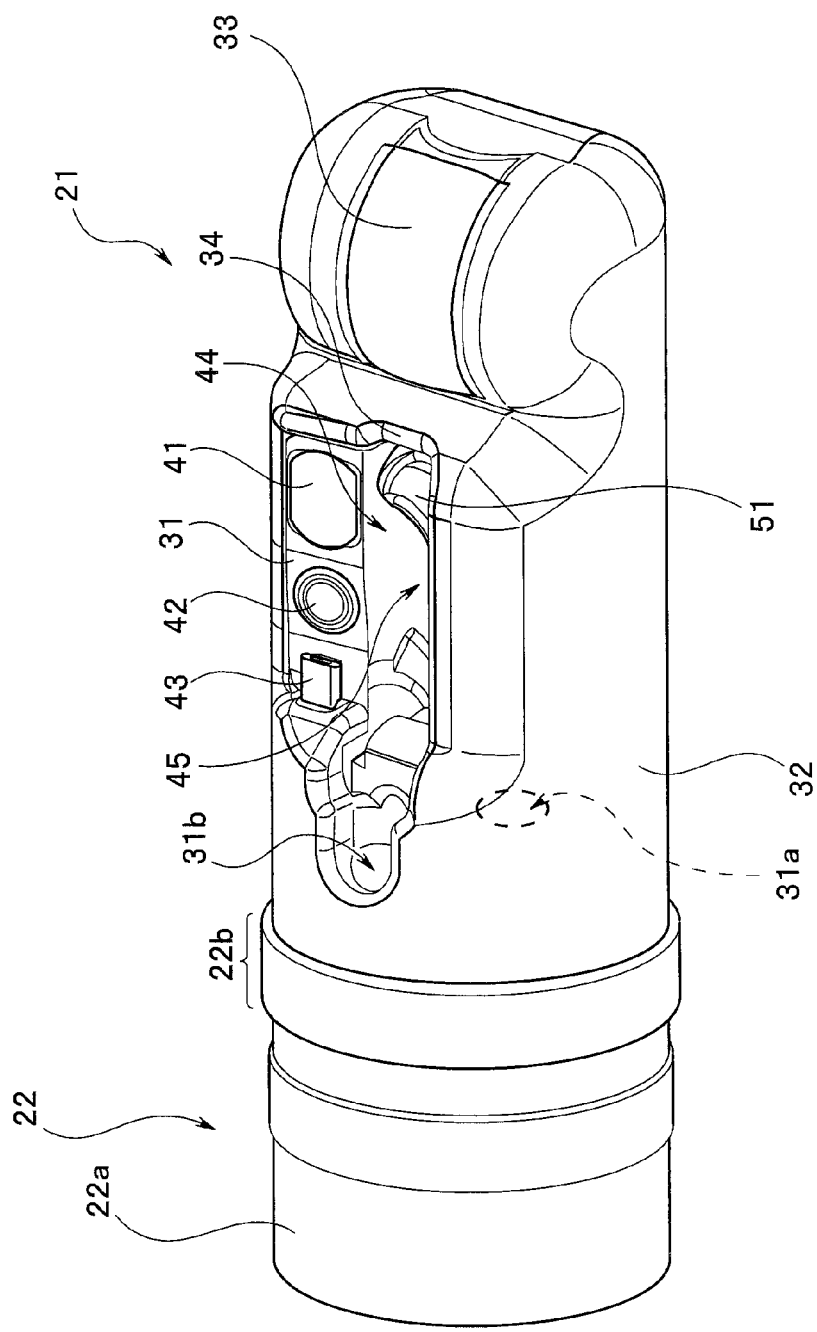
FIG. 2 is a perspective view of a distal end portion 21 according to the first embodiment of the present invention when a raising stand is laid.
Figure 3:
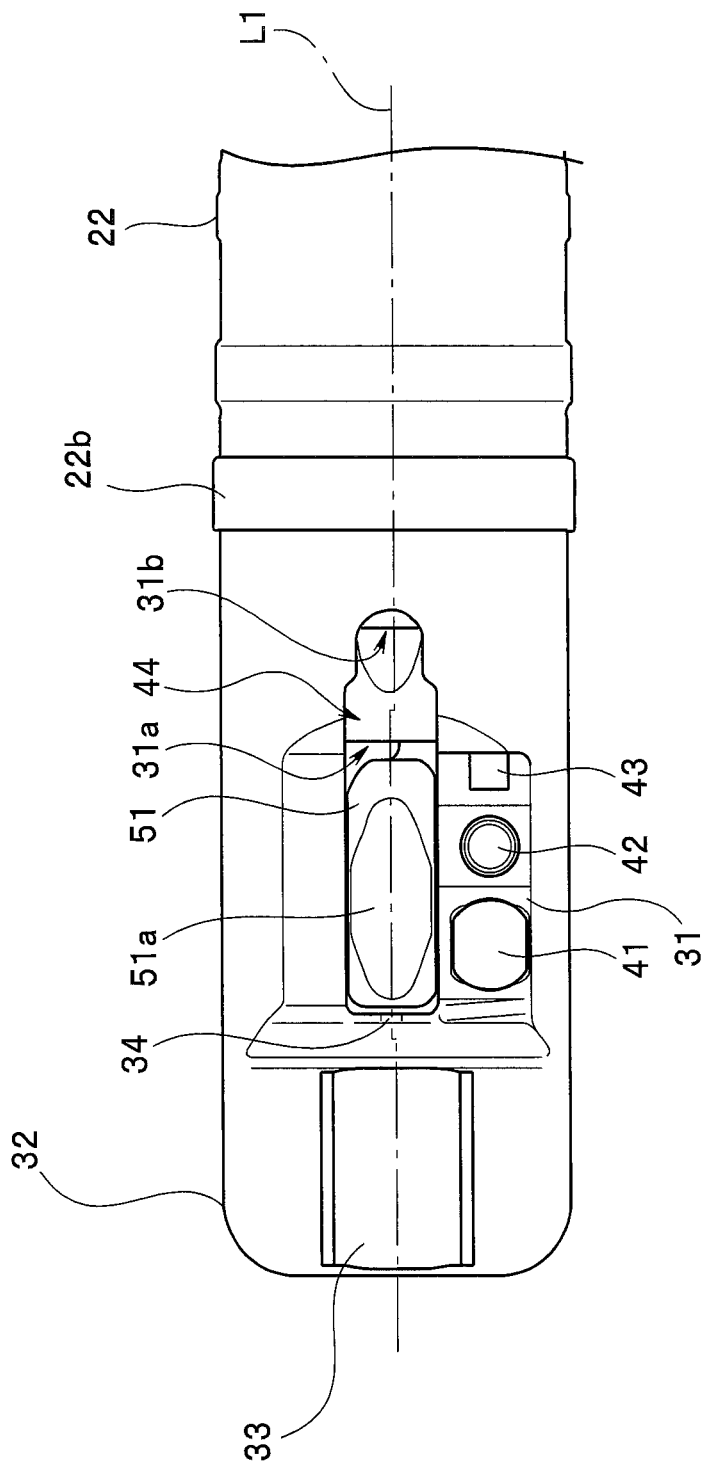
FIG. 3 is a plan view of the distal end portion 21 according to the first embodiment of the present invention when the raising stand is laid.
Figure 4:
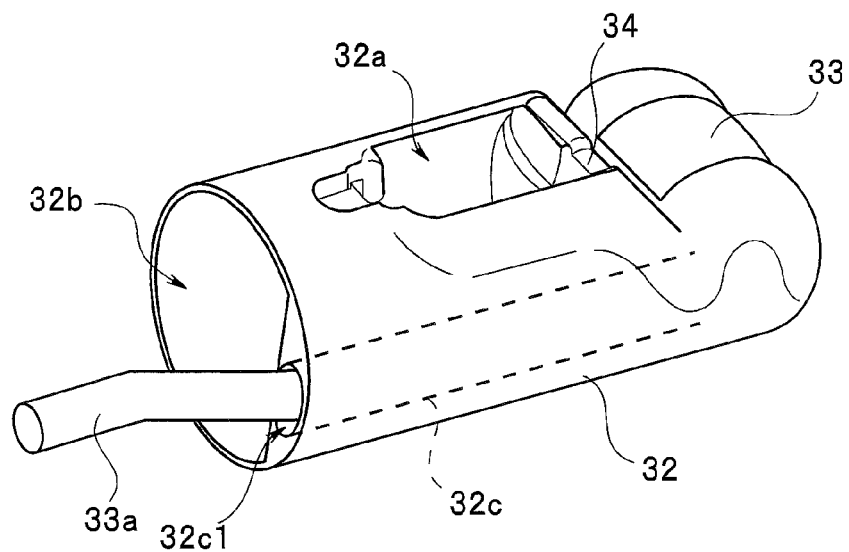
FIG. 4 is a perspective view of a cover member according to the first embodiment of the present invention seen in a diagonal direction on a proximal end side.
Figure 5:
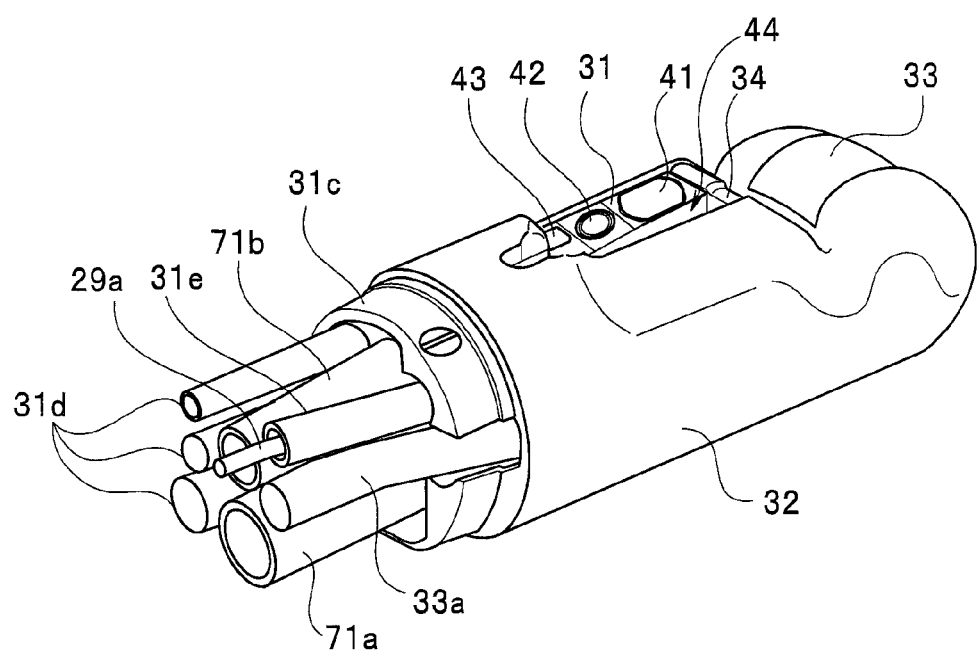
FIG. 5 is a perspective view of the distal end portion 21 according to the first embodiment of the present invention in which the distal end rigid portion member is fitted into the cover member seen in a diagonal direction on the proximal end side.

FIG. 2 is a perspective view of the distal end portion 21 when a raising stand is in a laid position. FIG. 3 is a plan view of the distal end portion 21 when the raising stand is laid. FIG. 4 is a perspective view of a cover member seen in a diagonal direction on a proximal end side. FIG. 5 is a perspective view of the distal end portion 21 in which the distal end rigid portion member is fitted into the cover member seen in the diagonal direction on the proximal end side.

The distal end portion 21 is configured by including a metallic distal end rigid member 31 and a cylindrical synthetic resin cover member 32 in which the distal end rigid member 31 is inserted. That is, the cover member 32 is attached so as to cover the distal end rigid member 31. Such a configuration ensures insulation of the distal end portion 21 and also allows the ultrasound transducer section to be reliably fixed. The cover member 32 is fixed to the distal end rigid member 31 by an adhesive.

As shown in FIG. 4, the distal end portion of the cylindrical cover member 32 is closed and an ultrasound vibration section 33 is accommodated within the distal end portion. The cover member 32 includes an elongated opening portion 32a formed on one side along an axial direction of the cylindrical cover member 32 and two opening portions 32b and 32c1 formed on a proximal end side.

As shown in FIG. 2, the proximal end portion of the distal end portion 21 is covered with a bending rubber member 22a which is a skin of the bending portion 22. The proximal end portion of the cover member 32 and the distal end portion of the bending portion 22 are coupled and fixed by a fixing section 22b such as a bobbin.

An ultrasound transducer section 33 including an ultrasound transducer is accommodated inside the distal end portion of the cover member 32 and a cable 33a of the ultrasound transducer section 33 passes through a cable duct 32c provided inside the cover member 32 as shown in FIG. 4 and extends from the opening portion 32c1 of the proximal end portion of the cover member 32. That is, the cover member 32 unites the cover that covers the distal end rigid member 31 and the cover that covers the ultrasound vibration section 33, and the cable 33a of the ultrasound transducer section 33 extends from the proximal end of the cover member 32. Such a cover member 32 can reduce the outer diameter of the distal end portion 21.

When the cover member 32 is attached so as to cover the distal end rigid member 31 to which various members such as an illumination lens are attached, as shown in FIG. 5, the illumination lens or the like is exposed from the opening portion 32a of the cover member 32 and the proximal end portion 31c of the distal end rigid member 31 protrudes from the opening portion 32b. Two channel tubes (hereinafter referred to as "channel tubes") 71a and 71b for inserting treatment instruments, the cable 33a of the ultrasound transducer section 33 and a duct 31e for a raising wire 29a extend from the proximal end portion 31c of the distal end rigid member 31, and other content group 31d such as a cable of an image pickup device, an illumination light guide and a cleaning duct also extend.

When the cover member 32 is attached to the distal end rigid member 31 as shown in FIG. 2, at the opening portion 32a of the cover member 32, an illuminating window 41, an observation window 42 and a cleaning nozzle 43 are arranged side by side and exposed along the axial direction of the insertion portion 11 from the distal end side of the insertion portion 11. The cleaning nozzle 43 is arranged so that cleaning water jetting from the opening portion of the cleaning nozzle 43 strikes surfaces of the observation window 42 and the illuminating window 41.

When the cover member 32 is attached to the distal end rigid member 31, part of the opening portion 32a is covered with part of the distal end rigid member 31 on which the illuminating window 41, the observation window 42 and the cleaning nozzle 43 are arranged. The other part of the opening portion 32a not covered with part of the distal end rigid member 31 on which the illuminating window 41 or the like is arranged forms an opening portion 44 from which the raising stand 51 protrudes when the raising stand 51 is raised.

A concave portion 45 is formed at the distal end portion 21 from the opening portion 44 toward the inside of the distal end rigid member 31. The concave portion 45 forms a space in which the raising stand 51 is accommodated. As will be described later, when the raising stand 51 is raised, the distal end portion of the raising stand 51 protrudes from the opening portion 44. That is, the distal end portion 21 of the insertion portion 11 has a concave portion formed on one side of the distal end portion 21, the concave portion being capable of accommodating the raising stand 51.

A convex portion 34 extending along a direction orthogonal to the insertion axis of the insertion portion 11 is formed between the ultrasound transducer 33 and the opening portion 44. The convex portion 34 constitutes a contact portion that contacts the side face of the treatment instrument TD1.

The raising operation and the laying operation of the raising stand 51 are performed by manipulation of the raising lever 29 of the operation portion 12. As described above, when the raising lever 29 is turned toward the predetermined first direction (arrow A1 direction), the raising stand 51 is raised and protrudes from the opening portion 44, and when the raising lever 29 is turned toward a direction opposite to the first direction (arrow A2 direction), the raising stand 51 is laid and accommodated in a concave portion 45. The manipulation of the raising lever 29 is transmitted to the distal end portion via the raising wire 29a.

Next, an inner structure of the distal end portion 21 will be described.

Figure 6:
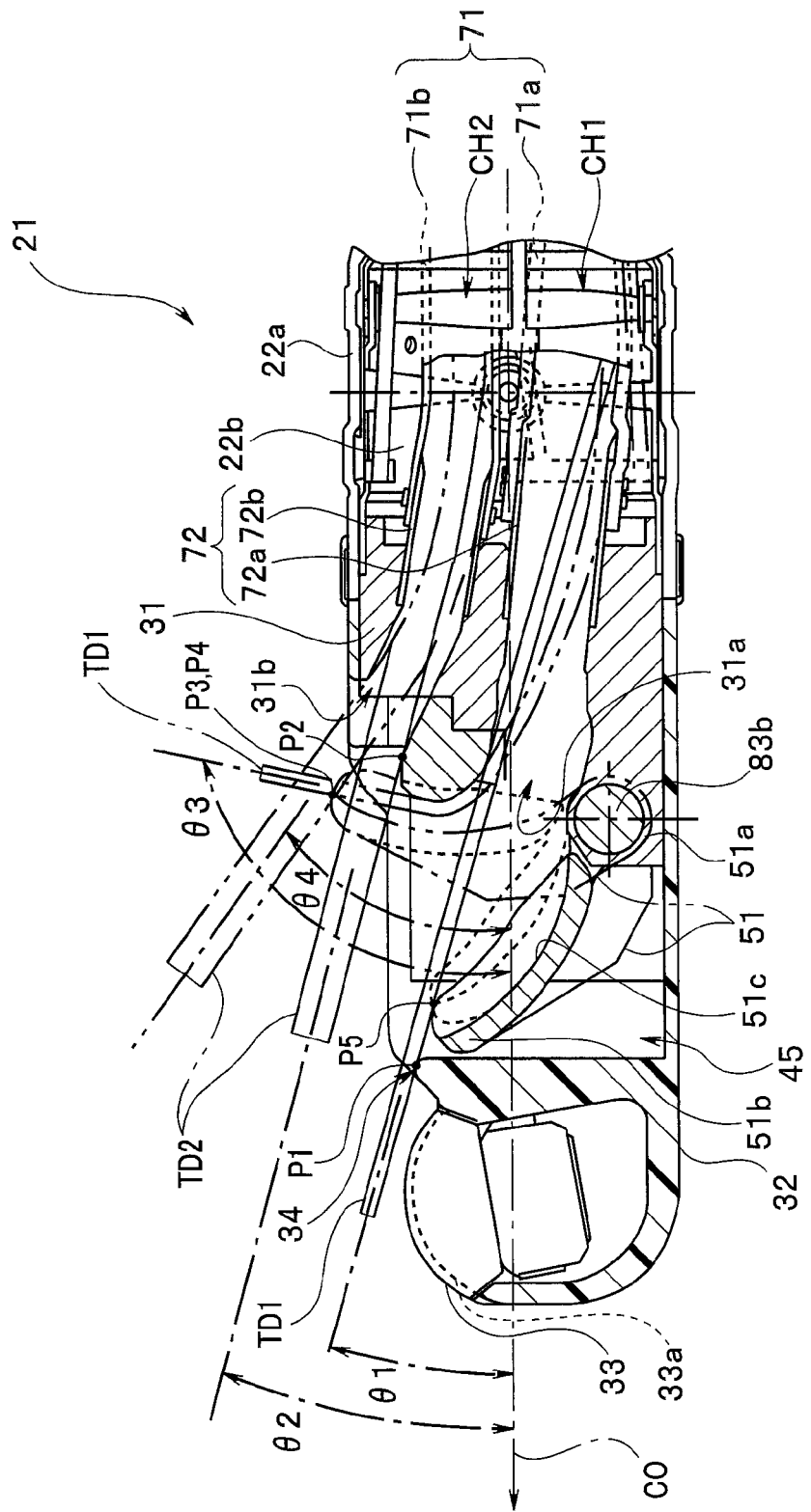
FIG. 6 is a cross-sectional view of the distal end portion 21 along a line L1 shown by a dotted line in FIG. 3.

FIG. 6 is a cross-sectional view of the distal end portion 21 along a line L1 shown by a dotted line in FIG. 3. As shown in FIG. 3, the single-dot dashed line L1 is a line along the insertion axis of the insertion portion 11, but is not a single straight line and the single-dot dashed line L1 is crank-shaped so that the cross-sectional view in FIG. 6 becomes a cross section that passes through the center line of the raising stand 51.

The ultrasound transducer section 33 is provided at the distal end portion 21 of the insertion portion 11. The ultrasound transducer 33a in the ultrasound transducer section 33 is provided at the distal end portion 21 of the insertion portion 11 and emits ultrasound sideward at a predetermined angle with respect to an insertion axis C0 of the insertion portion 11.

As shown in FIG. 6, the proximal end portion of the distal end rigid member 31 engages with the distal end portion of a bending piece 22b of the bending portion 22, and the distal end rigid member 31 and the bending piece 22b are fixed by a fastening device (not shown). Two channel tubes 71: channel tubes 71a and 71b are arranged inside the insertion portion 11. One of the two channel tubes 71 is the channel tube 71a for inserting a treatment instrument such as cannula to be used when ERCP is performed and forms an ERCP channel CH1. The other of the two channel tubes 71 is the channel tube 71b for inserting a treatment instrument which is a puncture apparatus to be used when EUS-FNA is performed and forms an EUS-FNA channel CH2.

The two channel tubes 71 are fixed to the distal end rigid member 31 via fastening pipe members 72. With the distal end portion of the channel tube 71a inserted into a predetermined one orifice of the distal end rigid member 31, extrapolated and fixed at an end of the fixed pipe 72a, the channel tube 71a is thereby connected to the distal end rigid member 31. Similarly, with the distal end portion of the channel tube 71b inserted into another predetermined orifice of the distal end rigid member 31, extrapolated and fixed at an end of the fixed pipe 72b, the channel tube 71b is connected to the distal end rigid member 31.

The channel CH1 formed of the channel tube 71a communicates with an opening portion 31a provided on a distal end side of the distal end rigid member 31. The channel CH2 formed of the channel tube 71b communicates with an opening portion 31b provided on a distal end side of the distal end rigid member 31.

As shown in FIG. 3 and FIG. 6, an opening portion 31a of the channel CH1 is formed on a bottom surface, side inside the concave portion 45 apart from the opening portion 44. That is, the opening portion 31a is disposed inside the concave portion 45 at the distal end portion 21 of the insertion portion 11.

An opening portion 31b of the channel CH2 is provided at a position in the vicinity of the opening portion 44 of the insertion portion 11 and different from the opening portion 31a, and farmed at a position above the opening portion 31a apart from the bottom surface of the concave portion 45. That is, the two opening portions 31a and 31b of the two channels at the distal end portion 21 are arranged side by side along the vertical direction toward the opening 44 from the bottom surface of the concave portion 45 when the insertion portion 11 is seen from the distal end side, that is, along a direction from the base of the concave portion 45 toward the opening portion 44.

The raising stand 51 is provided so as to be rotatable around a predetermined axis inside the distal end rigid member 31. A shaft 83b which is a rotation shaft member is rotatably fixed around an axis of the distal end rigid member 31, the raising stand 51 is pivotally supported by the shaft 83b and provided in the distal end rigid member 31 so as to be rotatable around a rotation axis of the shaft 83b. The shaft 83b pivotally supports the raising stand 51 at a proximal end portion 51a of the raising stand 51.

The raising stand 51 is a bar-like member bent from the proximal end portion 51a toward a distal end portion 51b. The raising stand 51 is provided inside the distal end rigid member 31 so that the distal end portion 51b of the raising stand 51 is bent toward the two opening portions 31a and 31b.

Furthermore, the raising stand 51 includes a contact surface 51c with which a treatment instrument comes into contact from the proximal end portion 51a along the distal end portion 51b on the two opening portion 31a and 31b sides. The contact surface 51c is a concave portion having an elongated curved surface formed from the proximal end portion 51a to the distal end portion 51b.

Figure 7:
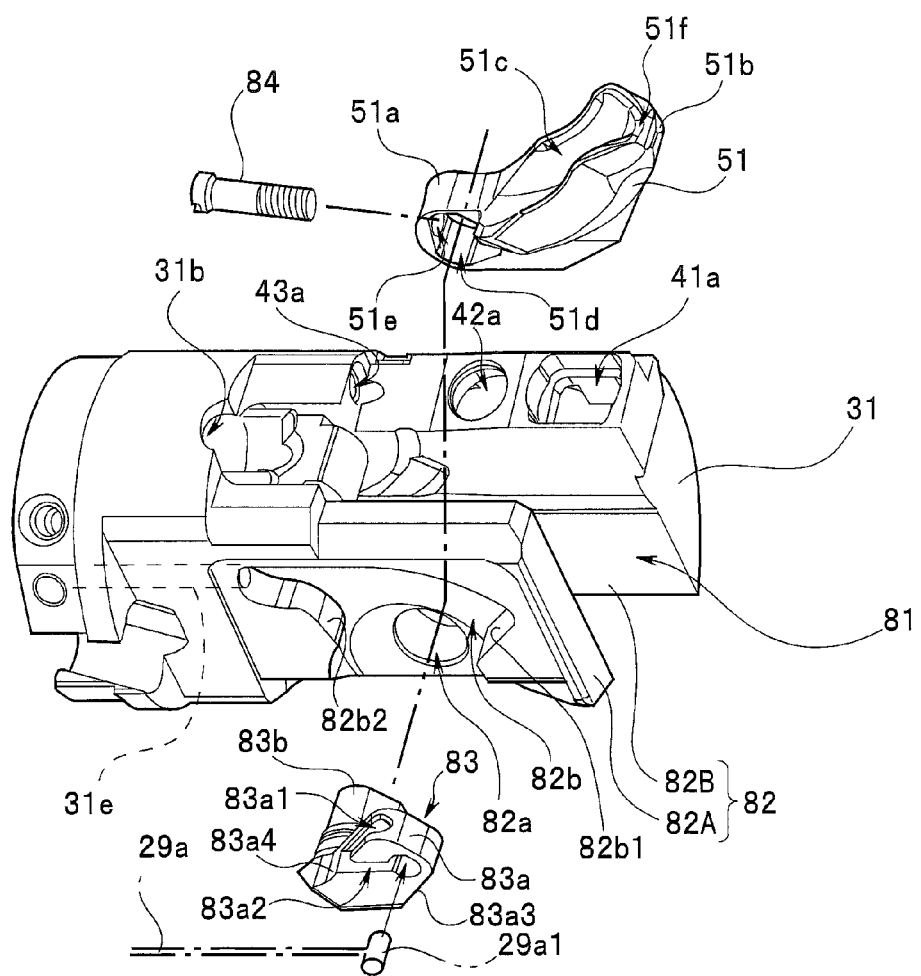
FIG. 7 is an exploded view for describing assembly of a raising stand 51 into a distal end rigid member 31 according to the first embodiment of the present invention.

FIG. 7 is an exploded view for describing an assembly of the raising stand 51 to the distal end rigid member 31. As shown in FIG. 7, the distal end rigid member 31 has a substantially columnar shape and includes a slit portion 81 which extends from the distal end side up to some midpoint.

As shown in FIG. 7, the distal end portion 51b of the raising stand 51 includes a contact portion 51f with which the side face of the treatment instrument comes into contact. The contact portion 51f includes a concave portion having a curved surface as shown in FIG. 7.

An orifice 82a is formed in one wall portion 82A of two wall portions 82 that form the slit portion 81 of the distal end rigid member 31. The slit portion 81 is formed such that the raising stand 51 is rotatable around a rotation axis of the shaft 83b within the slit portion 81.

Note that opening portions 41a, 42a and 43a for mounting respective members of the illuminating window 41, the observation window 42 and the cleaning nozzle 43 are formed in the other wall portion 82B of the two wall portions 82.

An orifice 51d is formed in the proximal end portion 51a of the raising stand 51 with which the shaft 83b of an engaging member 83 engages with which the raising wire 29a, which will be described later, engages. Furthermore, an orifice 51e is also formed in the proximal end portion 51a of the raising stand 51 through which a screw 84, which will be described later, is inserted.

The engaging member 83 is L-shaped and includes an engaging portion 83a with which one end of the raising wire 29a engages, the other end of the raising wire 29a being fixed to the raising lever 29, and the shaft 83b. The shaft 83b has such a shape that the shaft 83b can be rotatably inserted into the orifice 82a. The other end of the raising wire 29a has an end portion 29a1 having an expanded diameter (not shown). The engaging portion 83a includes an engaging groove portion 83a1 and a groove 83a2. The engaging groove portion 83a1 is an engaging portion that prevents the raising wire 29a from coming off even when the raising wire 29a is pulled. The groove 83a2 is a groove through which the distal end portion 29a1 of the raising wire 29a is fitted into the engaging groove portion 83a1.

A concave portion 82b is formed in the surface opposite to the slit portion 81 of the wall portion 82A and the orifice 82a is formed in the concave portion 82b.

With the distal end portion of the shaft 83b inserted in the orifice 82a engaging with the orifice 51d of the proximal end portion 51a of the raising stand 51 in the slit portion 81, the screw 84 is screwed into a side wall of the shaft 83b through the orifice 51e from a direction orthogonal to the axis of the shaft 83b, the raising stand 51 is integrated with the engaging member 83 and becomes rotatable around the shaft 83b.

As described above, the distal end portion 29a1 of the raising wire 29a engages with the engaging groove portion 83a1 of the engaging member 83 and the raising wire 29a is inserted into the duct 31e fixed to the distal end rigid member 31.

Therefore, when the raising wire 29a moves forward or backward within the insertion portion 11 according to the operation of the raising lever 29, the engaging member 83 to which the raising wire 29a is connected rotates around the shaft 83b inserted into the orifice 82a according to the forward or backward movement. The raising stand 51 integrally fixed to the shaft 83b also rotates according to the rotation of the shaft 83b.

Furthermore, the concave portion 82b includes two stopper portions 82b1 and 82b2. As shown in FIG. 7, when the raising stand 51 is laid, the stopper portion 82b1 comes into contact with one side wall 83a3 of the engaging member 83 and regulates the movement of the engaging member 83 so that the raising stand 51 does not rotate further in the laying direction.

Similarly, as shown in FIG. 7, when the raising stand 51 is raised, the stopper portion 82b2 comes into contact with one side wall 83a4 of the engaging member 83 and regulates the movement of the engaging member 83 so that the raising stand 51 does not rotate further in the raising direction.

Figure 8:
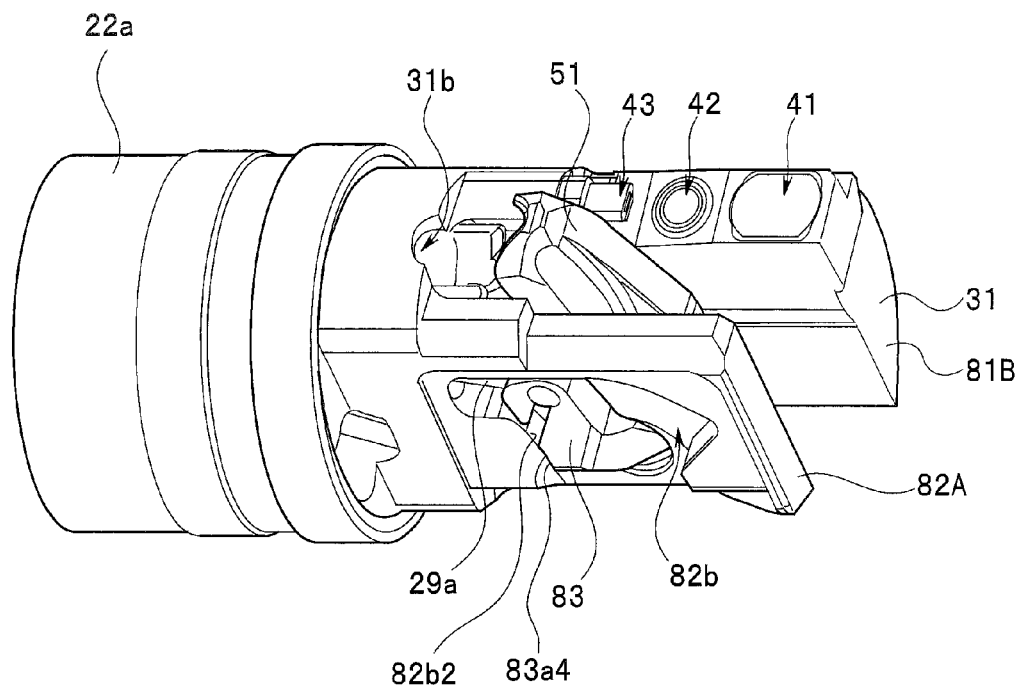
FIG. 8 is a perspective view of the distal end rigid member 31 when a raising lever 29 according to the first embodiment of the present invention is turned toward a predetermined first direction (arrow A1 direction)

FIG. 8 is a perspective view of the distal end rigid member 31 when the raising lever 29 is turned in a predetermined first direction (arrow A1 direction). That is, FIG. 8 illustrates the raising stand 51 in a raised position. In FIG. 8, the side wall 83a4 of the engaging member 83 is in contact with the stopper portion 82b2 of the concave portion 82b.

Figure 9:
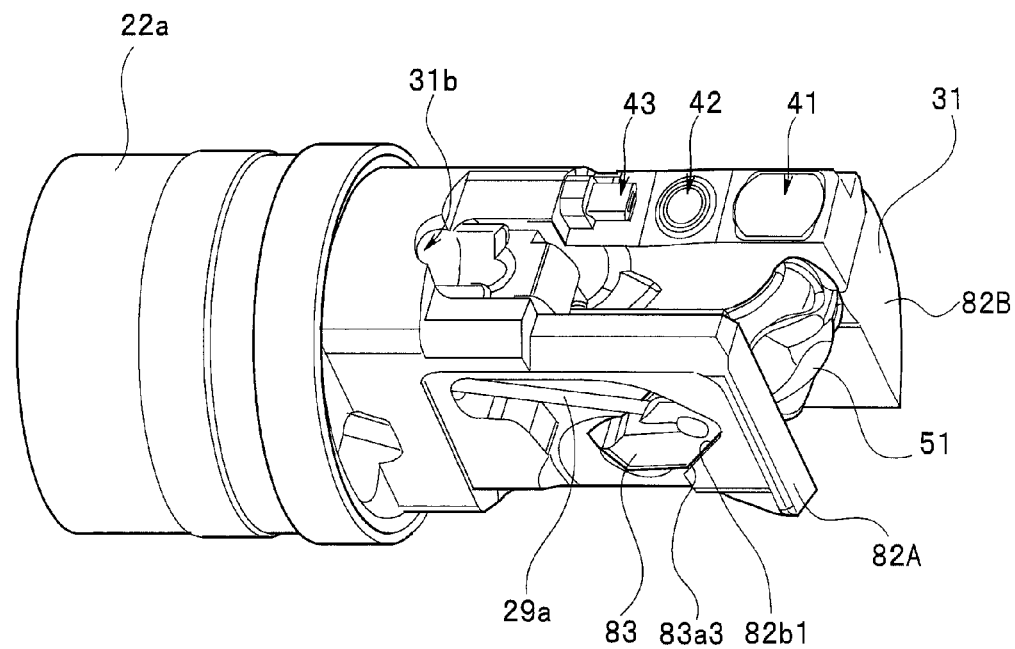
FIG. 9 is a perspective view of the distal end rigid member 31 when the raising lever 29 according to the first embodiment of the present invention is turned toward a direction opposite to the first direction (arrow A2 direction)
Figure 10:
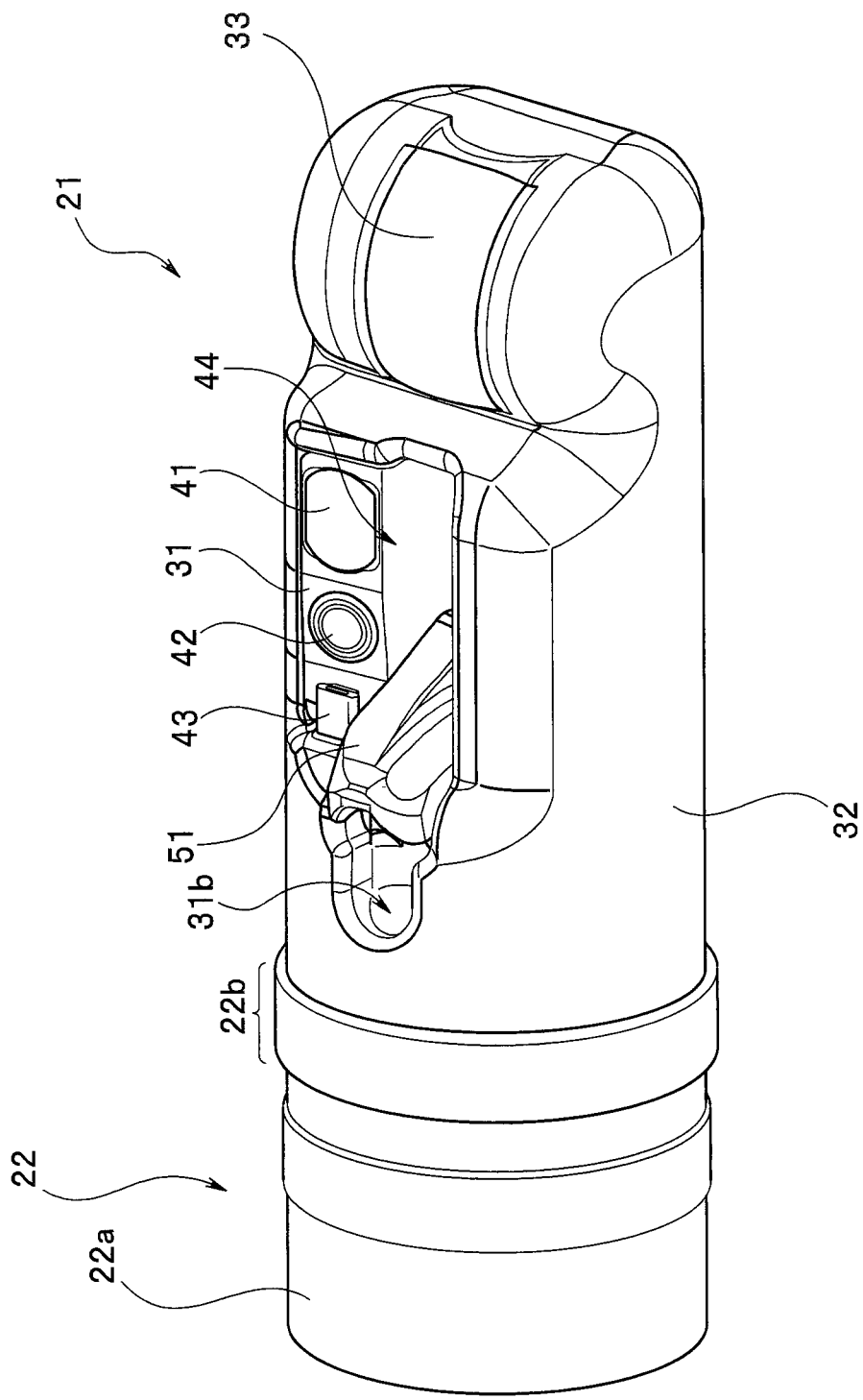
FIG. 10 is a perspective view of the distal end portion 21 when the raising lever 29 according to the first embodiment of the present invention is turned toward the first direction (arrow A1 direction)

FIG. 9 is a perspective view of the distal end rigid member 31 when the raising lever 29 is turned in a direction opposite to the first direction (arrow A2 direction). FIG. 10 is a perspective view of the distal end portion 21 when the raising lever 29 is turned in the first direction (arrow A1 direction). In FIG. 9, the side wall 83a3 of the engaging member 83 is in contact with the stopper portion 82b1 of the concave portion 82b. FIG. 9 illustrates the raising stand 51 in a laid position and FIG. 10 illustrates the raising stand 51 in a raised position.

As described above, the raising stand 51 is provided at the distal end portion 21 of the insertion portion 11 and is movable between the raised position where the raising stand 51 approximates to the opening portion 31a and opening portion 31b and the laid position where the raising stand 51 is away from the opening portion 31a and opening portion 31b.

As described above, the treatment instrument is inserted from each forceps port 25a, 25b located at the channel opening setting portion 25 of the operation portion 12. The ERCP treatment instrument is inserted from the forceps port 25b and the EUS-FNA treatment instrument is inserted from the forceps port 25b.

(Operation)

Next, operation of the endoscope 3 will be described using FIG. 6.

As shown by a solid line in FIG. 6, when the raising stand 51 is in a laid position, if the treatment instrument TD1 such as cannula is inserted into the channel CH1 from the forceps port 25b, the distal end portion of the treatment instrument TD1 passes through the channel CH1 and comes out of the opening portion 31a, and comes into contact with the contact surface 51c first, and then moves toward the distal end portion 51b along the contact surface 51c. When the treatment instrument TD1 is further pushed into the forceps port 25b, the distal end portion of the treatment instrument TD1 goes beyond the distal end portion 51b of the raising stand 51, further goes beyond the convex portion 34 between the opening portion 44 and the ultrasound transducer section 33 and protrudes from the opening portion 44.

The treatment instrument TD1 at this time protrudes from the opening portion 44 at an angle θ1 with respect to the distal end direction of an insertion axis C0 of the insertion portion 11. The angle θ1 is defined by elasticity of the treatment instrument TD1 itself, the position of the opening portion 31a and the height of the convex portion 34 which is the contact portion. In the case of FIG. 6, since the side face of the treatment instrument TD1 is in contact with a point P1 of the convex portion 34, the angle θ1 is substantially defined by the position of the treatment instrument TD1 and the position of the point P1 in the opening portion 31a.

As shown by a solid line in FIG. 6, when the raising stand 51 is in a laid position, if the treatment instrument TD2 such as a puncture apparatus is inserted into the channel CH2 from the forceps port 25a, the distal end portion of the treatment instrument TD2 moves along the inner wall of the channel CH2. When the treatment instrument TD2 is further pushed into the forceps port 25a, the distal end portion of the treatment instrument TD2 passes through the channel CH2, comes out of the opening portion 31b and protrudes from the opening portion 44 without touching the raising stand 51.

The treatment instrument TD2 at this time protrudes from the opening portion 44 at an angle θ2 with respect to the distal end direction of the insertion axis C0 of the insertion portion 11. The angle θ2 is defined by elasticity of the treatment instrument TD2 itself, the position of the opening portion 31b and an inner wall shape of the channel CH2 in the vicinity of the opening portion 31b. In the case of FIG. 6, since the side face of the treatment instrument TD2 is in contact with the point P2 of the opening portion 31b, the angle θ2 is substantially defined by the position of the treatment instrument TD2 and the position of the point P2 in the opening portion 31a.

Note that here, the treatment instrument TD1 protrudes forward at the angle θ1 with respect to the distal end direction of the insertion axis C0 and the angle θ1 is defined by elasticity of the treatment instrument TD1 itself, the position of the opening portion 31a and the height of the convex portion 34, but the height of the convex portion 34 may be lowered so that the treatment instrument TD1 comes into contact with the distal end portion 51b of the raising stand 51 or the height of the distal end portion 51b from the bottom surface of the concave portion 45 when the raising stand 51 is in a laid position may be raised. In that case, the angle θ1 is defined by elasticity of the treatment instrument TD1 itself, the position of the opening portion 31a and the height of the distal end portion 51b, and the treatment instrument TD1 does not touch the ultrasound transducer section 33.

In that case, in FIG. 6, the side face of the treatment instrument TD1 does not come into contact with the convex portion 34 and the side face of the treatment instrument TD1 comes into contact with the raising stand 51 at a point P5 of the distal end portion 51b of the raising stand 51 shown by a dotted line.

That is, the raising stand 51 may be configured so that when the raising stand 51 is in a laid position, the side face of the treatment instrument TD1 does not contact the surface of the ultrasound transducer section 33 including the ultrasound transducer and the treatment instrument TD1 protrudes from the opening portion 31a.

When the raising stand 51 is in a raised position as shown by a two-dot dashed line in FIG. 6, the protruding directions of the treatment instruments TD1 and TD2 are changed by the raising stand 51.

When the distal end portion of the treatment instrument TD1 such as a cannula passes through the channel CH1, comes out of the opening portion 31a and then the raising lever 29 is raised, the raising stand 51 is raised as shown by a two-dot dashed line in FIG. 6, and the protruding direction of the distal end portion of the treatment instrument TD1 is changed. The two-dot dashed line in FIG. 6 shows a state in which the raising stand 51 is raised to a maximum. The maximum raising angle of the treatment instrument TD1 is an angle θ3 with respect to the distal end direction of the insertion axis C0 of the distal end portion 21. The angle θ3 is defined by elasticity of the treatment instrument TD1 itself, the shape of the opening portion 31a and the shape of the distal end portion 51b of the raising stand 51. In the case of FIG. 6, since the side face of the treatment instrument TD1 is in contact with a point P3 on the contact portion 51f of the distal end portion 51b of the raising stand 51, the angle θ3 is substantially defined by the position of the treatment instrument TD1 at the opening portion 31a and the position of the point P3.

When the distal end portion of the treatment instrument TD2 such as a puncture apparatus passes through the channel CH2, comes out of the opening portion 31b and then the raising lever 29 is raised, the raising stand 51 is raised as shown by a two-dot dashed line in FIG. 6, and the protruding direction of the distal end portion of the treatment instrument TD2 is changed. A maximum raising angle of the treatment instrument TD2 is an angle θ4 with respect to the distal end direction of the insertion axis C0 of the distal end portion 21. The angle θ4 is defined by elasticity of the treatment instrument TD2 itself, the position of the opening portion 31b, the inner wall shape of the channel CH2 in the vicinity of the opening portion 31b and the shape of the distal end portion 51b of the raising stand 51. In the case of FIG. 6, since the side face of the treatment instrument TD2 is in contact with a point P4 of the opening portion 31b, the angle θ4 is substantially defined by the position of the treatment instrument TD2 and the position of the point P4 in the opening portion 31b.

Note that in FIG. 6, the point P3 and the point P4 are shown at the same position, but strictly speaking, the positions of the point P3 and point P4 are different.

As described above, the contact portion 51f is provided at the distal end portion 21, comes into contact with the treatment instrument TD1 protruding from the opening portion 31a at the point P3, causes the treatment instrument TD1 to extend in a direction of the angle θ3, is provided on the raising stand 51, comes into contact with the treatment instrument TD2 protruding from the opening portion 31b at the point P4 and causes the treatment instrument TD2 to extend in a direction of the angle θ4 different from the direction of the angle θ3.

In the above example in particular, when the raising stand 51 is in a raised position and the treatment instrument TD1 protrudes from the opening portion 31a, the side face of the treatment instrument TD1 comes into contact with the contact portion 51f at the point P3. Furthermore, when the raising stand 51 is in a raised position and the treatment instrument TD2 protrudes from the opening portion 31b, the side face of the treatment instrument TD2 comes into contact at the point P4. The contact portion at the point P3 and the contact portion at the point P4 in the contact portion 51f are at substantially the same position at the end portion of the raising stand 51.

The angle θ3 is 90 degrees or more and 130 degrees or less, and preferably from 100 to 110 degrees. The angle θ4 is 10 degrees or more and 40 degrees or less, and preferably from 30 to 35 degrees.

Figure 11:
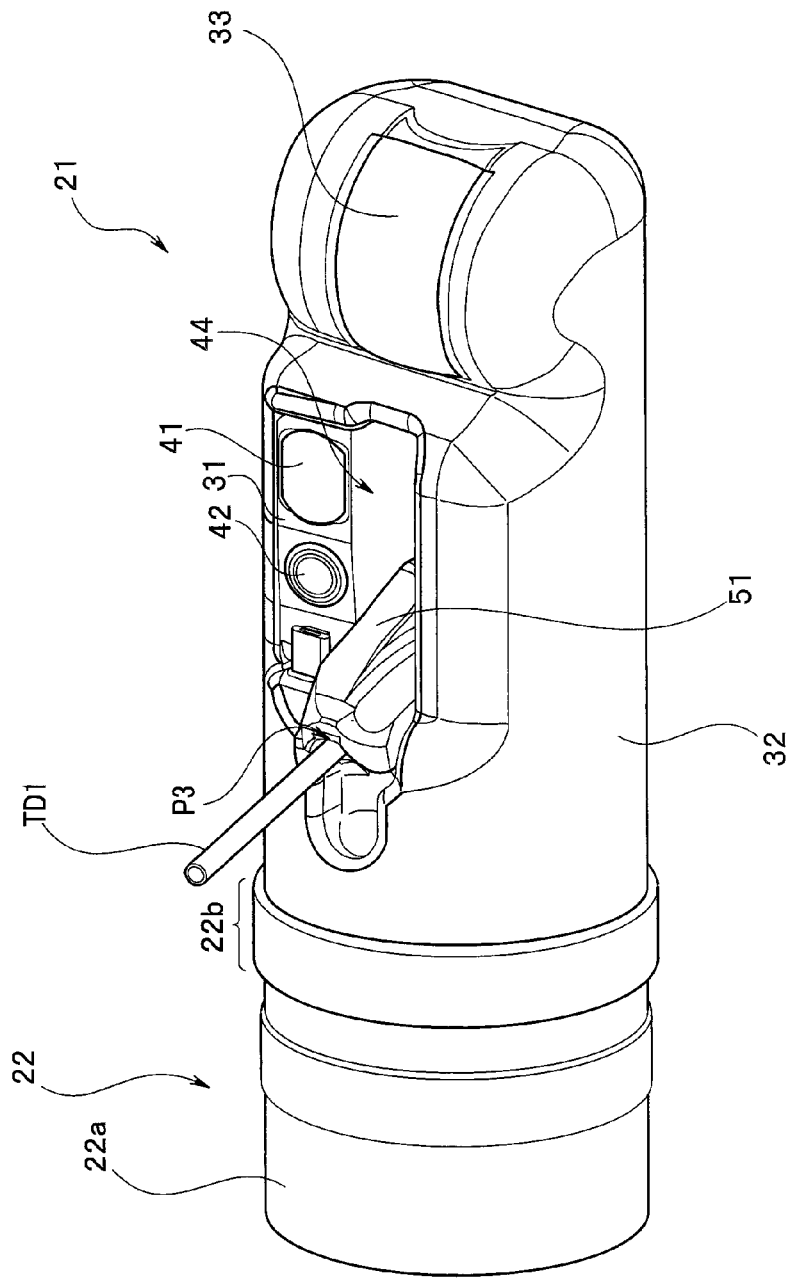
FIG. 11 is a perspective view of the distal end portion 21 illustrating the distal end portion of the treatment instrument TD1 protruding from an opening portion 44 when the raising stand 51 according to the first embodiment of the present invention is in a maximum raised position.
Figure 12:
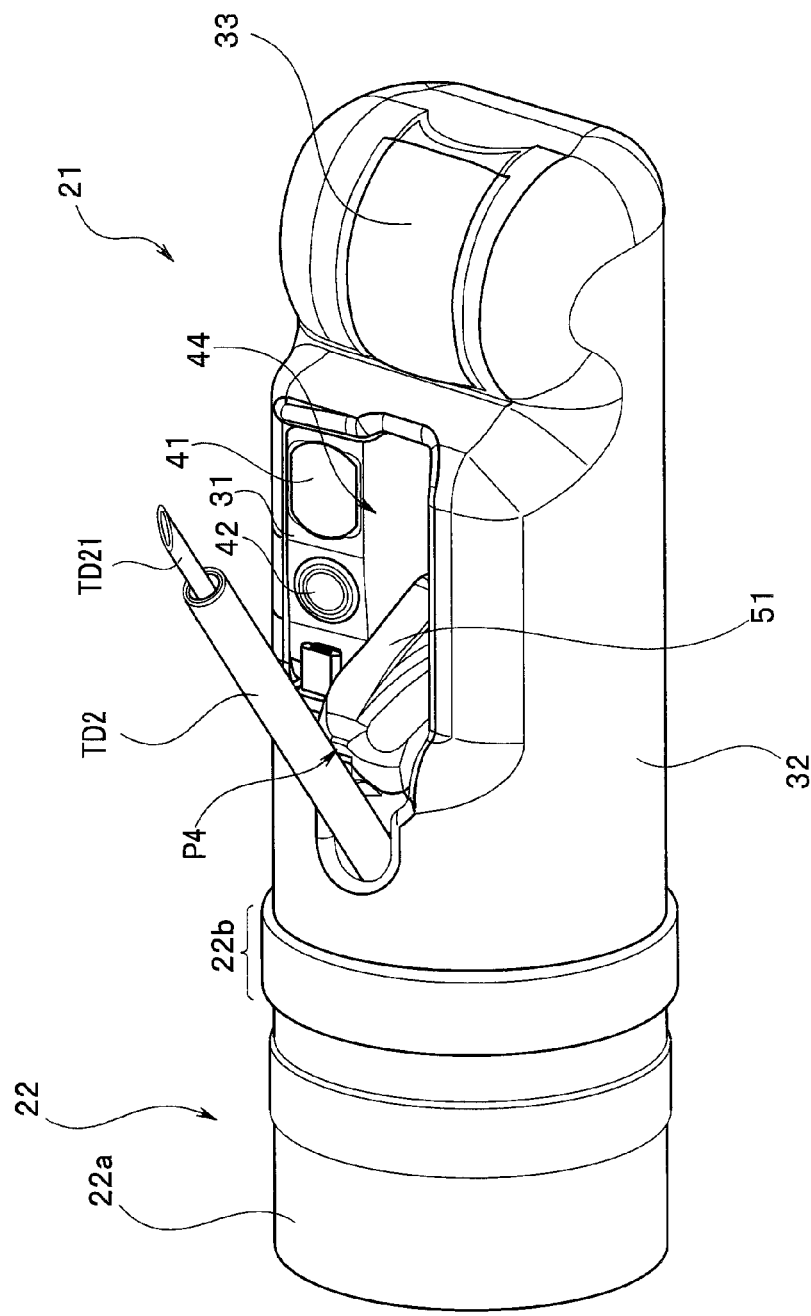
FIG. 12 is a perspective view of the distal end portion 21 illustrating the distal end portion of the treatment instrument TD2 protruding from the opening portion 44 when the raising stand 51 according to the first embodiment of the present invention is in a maximum raised position.

FIG. 11 is a perspective view of the distal end portion 21 illustrating a state in which the distal end portion of the treatment instrument TD1 protrudes from the opening portion 44 when the raising stand 51 is in a maximum raised position. FIG. 12 is a perspective view of the distal end portion 21 illustrating a state in which the distal end portion of the treatment instrument TD2 protrudes from the opening portion 44 when the raising stand 51 is in a maximum raised position. In FIG. 12, the treatment instrument TD2 is a puncture apparatus from which a needle TD21 protrudes.

For example, when the operator inserts the endoscope 3 into the stomach and performs a biopsy of the pancreas while watching an ultrasound image, the operator can perform the biopsy through the stomach wall by manipulating the raising lever 29 and using the treatment instrument TD2 which is a puncture apparatus. When a lesioned part is found in the head of pancreas, bile duct or the like from an ultrasound image, and the operator determines that ERCP is necessary, the operator inserts the treatment instrument TD1 from the forceps port 25b instead of the treatment instrument TD2 without pulling out the endoscope 2, manipulates the raising lever 29, and can perform ERCP by inserting a cannula or the like from the papilla.

As described above, according to the present embodiment, the distal end rigid portion of the insertion portion need not be further extended and it is possible to perform both endoscopic retrograde cholangiopancreatography (ERCP) and endoscopic ultrasound-guided fine needle aspiration (EUS-FNA) using one ultrasound endoscope.

(Second Embodiment)

In the first embodiment, when the distal end portion 21 is seen from the distal end side, the two opening portions of the two channels in the distal end portion 21 are arranged along a direction from the bottom surface of the concave portion 45 toward the opening 44, that is, arranged side by side along the vertical direction. In the second embodiment, however, when the distal end portion 21 is seen from the distal end side, the two opening portions of the two channels in the distal end portion 21 are provided along a diagonal direction at a predetermined angle with respect to a direction from the bottom surface of the concave portion 45 toward the opening 44. That is, according to the second embodiment, in a plan view of the opening portion of the distal end portion of the insertion portion, the two opening portions of the two channels are arranged shifted in a direction orthogonal to the insertion axis of the distal end portion.

Note that in the present embodiment, the same components as the components in the first embodiment are assigned the same reference numerals and description thereof will be omitted.

Figure 13:
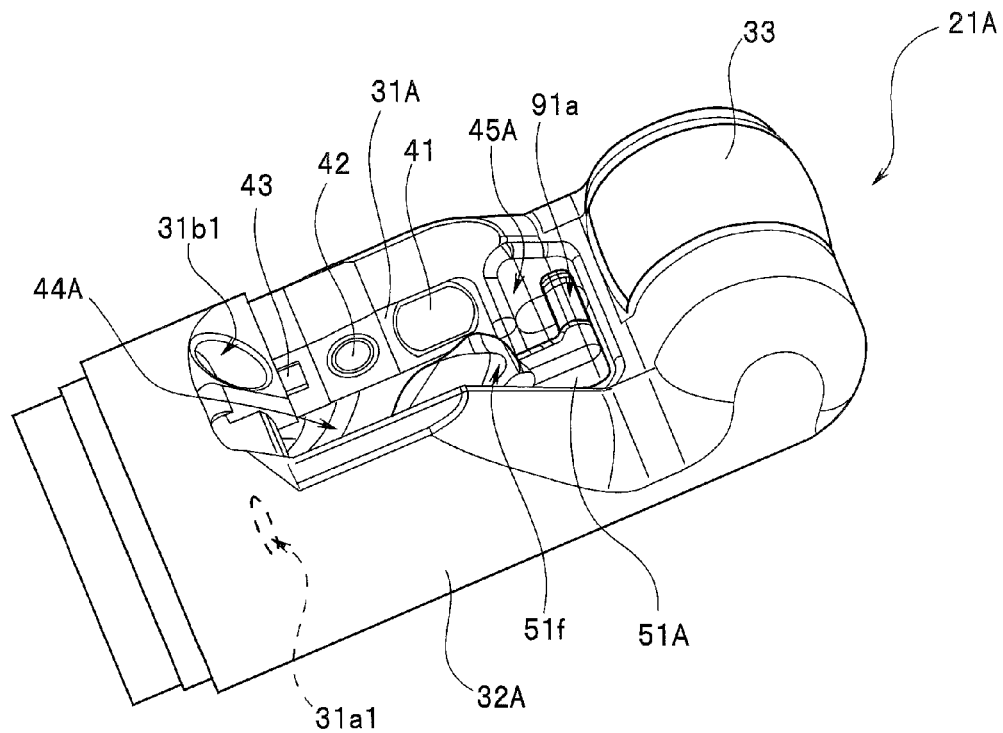
FIG. 13 is a perspective view of a distal end portion of an endoscope according to a second embodiment of the present invention.
Figure 14:
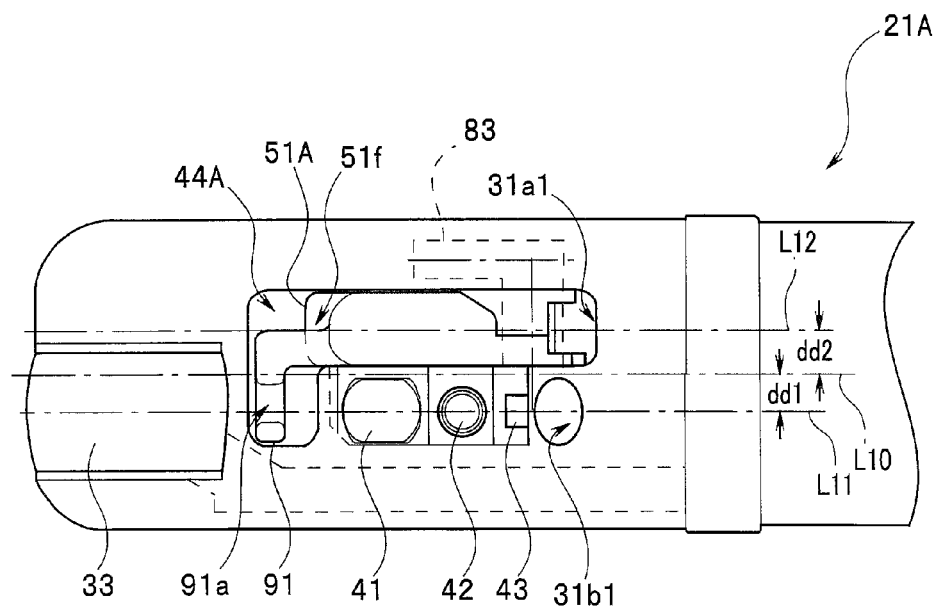
FIG. 14 is a plan view of the distal end portion of the endoscope according to the second embodiment of the present invention.

FIG. 13 is a perspective view of a distal end portion of an endoscope of the present embodiment. FIG. 13 is a perspective view of a distal end portion 21A when the raising lever 29 is turned in a direction opposite to the first direction (arrow A2 direction). FIG. 14 is a plan view of the distal end portion of the endoscope of the present embodiment. The distal end portion 21A of the present embodiment is also configured by including a cover member 32A and a distal end rigid member 31A covered with the cover member 32A.

As shown in FIG. 13 and FIG. 14, an opening portion 44A through which the raising stand 51A protrudes or retracts is provided on one side face of the distal end portion 21A and the opening portion 44A is L-shaped in a plan view. Furthermore, the distal end portion 21A includes a concave portion 45A according to the shape of the opening portion 44A inside the distal end rigid member 31A. An opening portion 31a1 of the channel CH1 formed of the channel tube 71a into which the treatment instrument TD1 is inserted is provided on the proximal end side in the concave portion 45A.

As shown in FIG. 14, in a plan view of the opening portion 44A, the ultrasound transducer section 33, the illuminating window 41, the observation window 42, the cleaning nozzle 43 and an opening portion 31b1 are arranged side by side along a straight line L11. The opening portion 31b1 is an opening portion of the channel CH2 formed of the channel tube 71b through which the treatment instrument TD2 is inserted. In a plan view of the opening portion 44A, the straight line L11 is deviated by a predetermined amount dd1 from a center line L0 which overlaps with an insertion axis C0 of the distal end portion 21A.

In the plan view of the opening portion 44A as shown in FIG. 14, a line L12 passing through the plane through which the center part of the distal end portion 51b of the raising stand 51A moves in the raising direction and parallel to the center line L0 is also deviated by the predetermined amount dd2 from the center line L0 of the distal end portion 21A.

That is, when the insertion portion 11 is seen from the distal end side, the opening portion 31a1 and the opening portion 31b1 are arranged along a direction having a predetermined angle with respect to a direction from the base of the concave portion 45A toward the opening portion 44A of the concave portion 45A.

Figure 15:
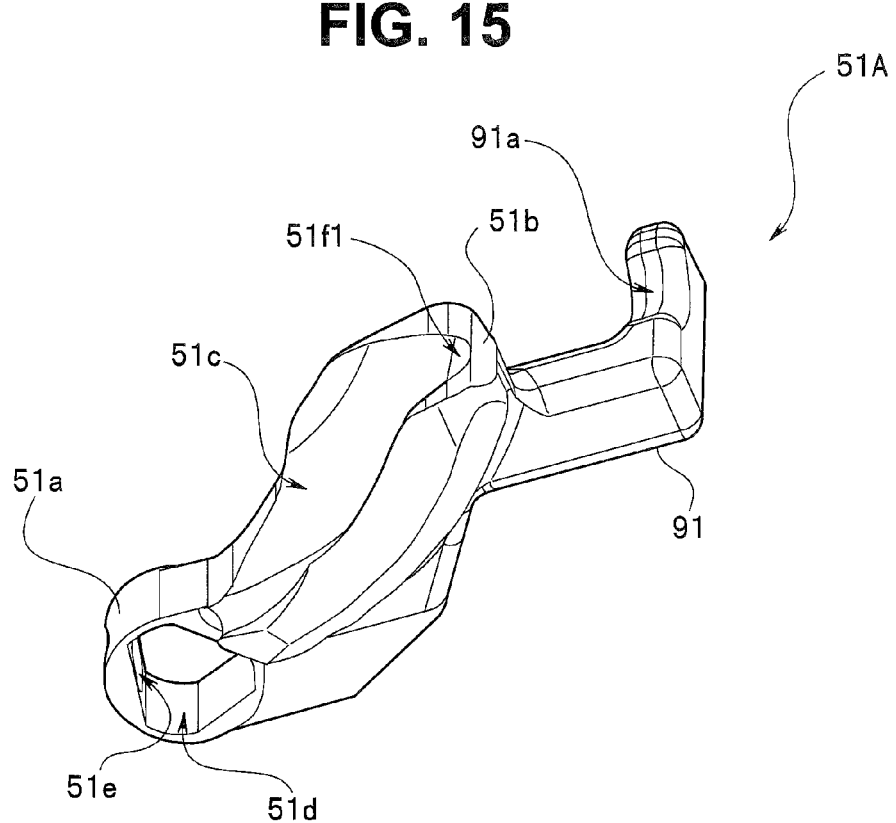
FIG. 15 is a perspective view of a raising stand 51A according to the second embodiment of the present invention.

FIG. 15 is a perspective view of the raising stand 51A. The raising stand 51A is a bar-like member bent from a proximal end portion 51a to a distal end portion 51b. As in the case of the raising stand 51 of the first embodiment, the raising stand 51A is provided inside the concave portion 45A of the distal end rigid member 31A so that the distal end portion 51b is bent toward the opening portion 31a1.

Furthermore, as in the case of the raising stand 51 of the first embodiment, in a raised position, the raising stand 51A has, on the opening portion 31a1 side, a contact surface 51c with which the treatment instrument TD1 comes into contact along the distal end portion 51b from the proximal end portion 51a. The contact surface 51c is a concave portion of an elongated curved surface formed from the proximal end portion 51a toward the distal end portion 51b.

Furthermore, the distal end portion 51b is provided with an L-shaped extending portion 91. The L-shaped extending portion 91 includes a contact portion 91a with which the side face of the treatment instrument TD2 comes into contact. As shown in FIG. 14, in a plan view of the opening portion 44A, the contact portion 91a of the extending portion 91 is arranged along the straight line L11 in the same way as the ultrasound transducer section 33, the illuminating window 41, the observation window 42, the cleaning nozzle 43, and the opening portion 31b1.

Figure 16:
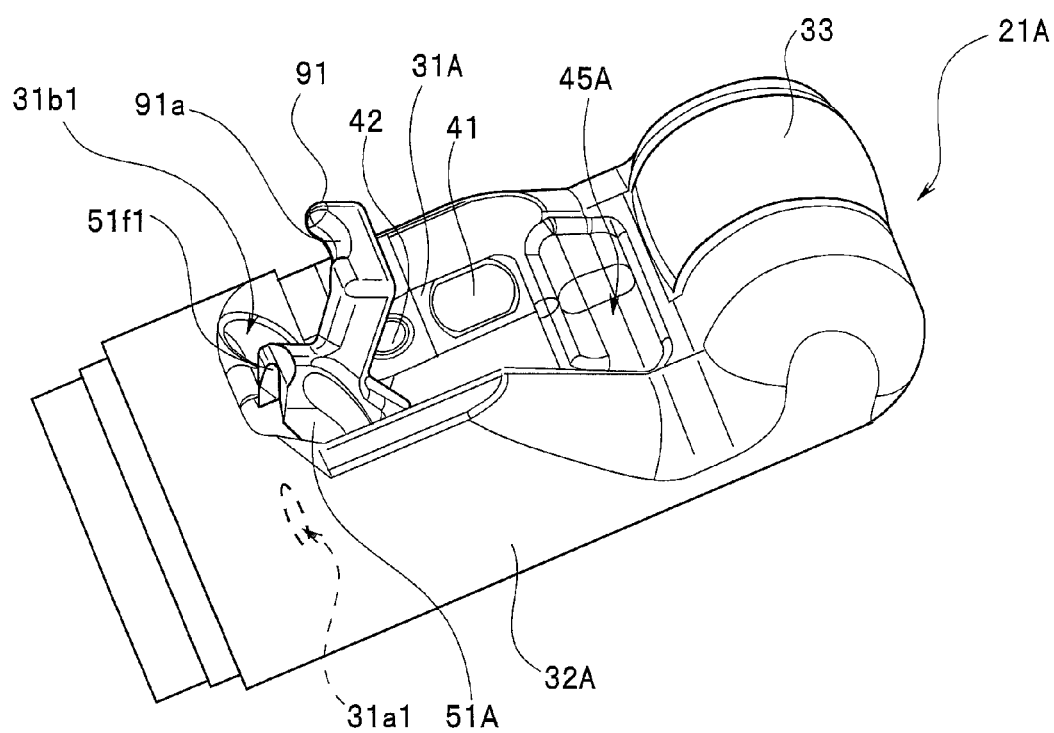
FIG. 16 is a perspective view of a distal end portion 21A when a raising lever 29 according to the second embodiment of the present invention is turned toward the first direction (arrow A1 direction)

FIG. 16 is a perspective view of the distal end portion 21A when the raising lever 29 is turned in the first direction (arrow A1 direction). As shown in FIG. 16, when the raising stand 51A is in a raised position, the raising stand 51A protrudes from the opening portion 44A.

Figure 17:
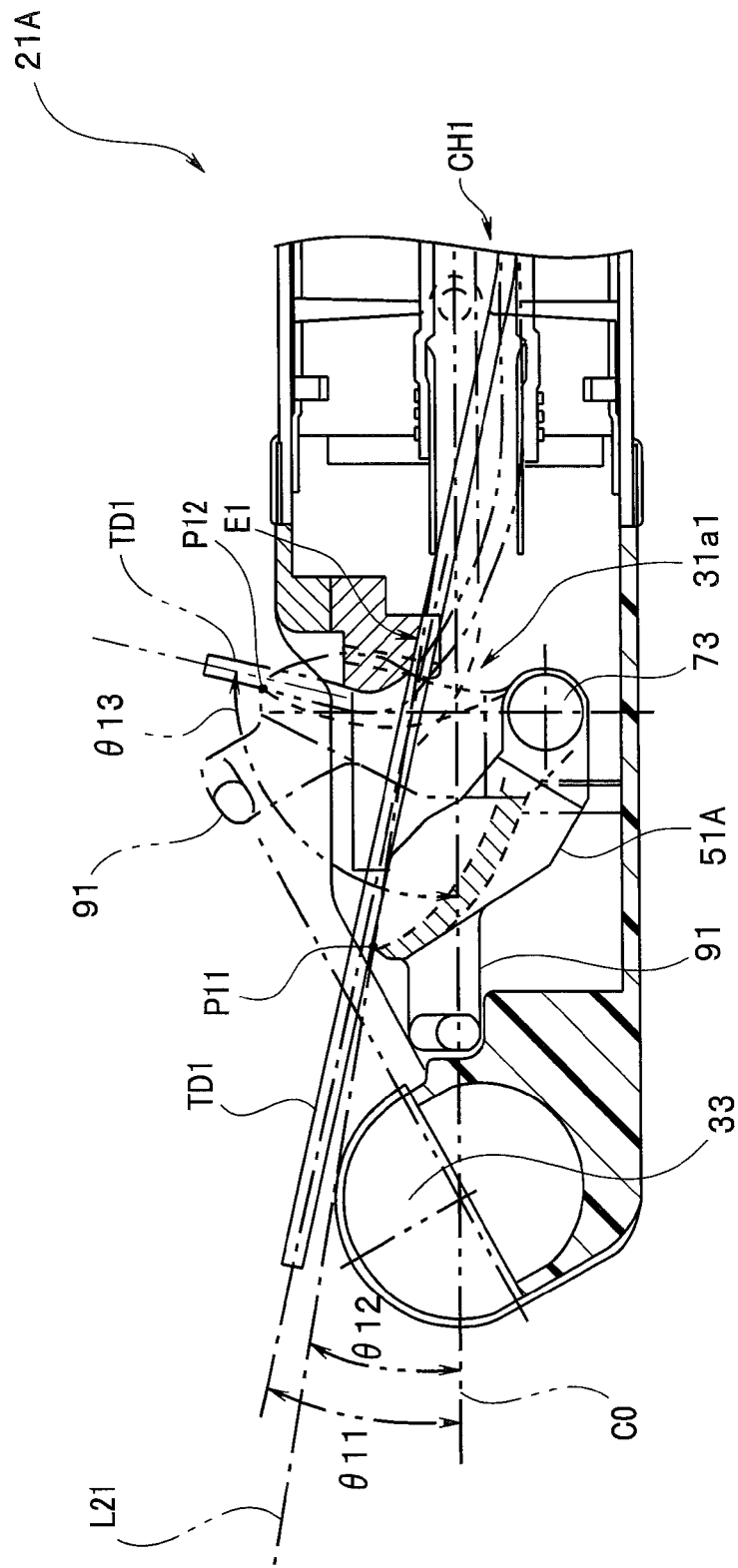
FIG. 17 is a cross-sectional view of the distal end portion 21A illustrating the treatment instrument TD1 protruding when the raising stand 51A according to the second embodiment of the present invention is raised and laid.

FIG. 17 is a cross-sectional view of the distal end portion 21A illustrating a protruding state of the treatment instrument TD1 when the raising stand 51A is raised and laid. FIG. 17 is a cross-sectional view along the straight line L12 in FIG. 14.

As shown in FIG. 17, the treatment instrument TD1 that protrudes from the opening portion 31a1 of the channel CH1 comes into contact at a point P11 of the contact portion 51f1 of the raising stand 51A as shown by a solid line and protrudes from the opening portion 44A.

When the raising stand 51A is in a laid position as shown by a solid line in FIG. 17, the distal end portion of the treatment instrument TD1 passes through the channel CH1, comes out of the opening portion 31a1, comes into contact with the contact surface 51c first, and then moves along the contact surface 51c toward the distal end portion 51b. When the treatment instrument TD1 is further pushed into the forceps port 25b, the distal end portion of the treatment instrument TD1 goes beyond the distal end portion 51b of the raising stand 51A and protrudes from the opening portion 44A.

The side face of the treatment instrument TD1 at this time comes into contact with the contact portion 51f and the treatment instrument TD1 protrudes from the opening portion 44A at an angle $\theta 11$ with respect to the distal end direction of the insertion axis C0 of the distal end portion 21. The angle $\theta 11$ is defined by elasticity of the treatment instrument TD1 itself, the position of the opening portion 31a1 and the position of the contact portion 51f1 of the distal end portion 51b.

In this case, the treatment instrument TD1 does not touch the ultrasound transducer section 33. This is because as shown in FIG. 17, the angle $\theta 11$ is greater than an angle $\theta 12$ formed by a tangent L21 contacting both an upside edge E1 of the opening portion 31a1 and the surface of the ultrasound transducer section 33 with respect to the distal end direction of the insertion axis C0 of the distal end portion 21.

That is, when the raising stand 51A is in a laid position, the raising stand 51 is configured such that the treatment instrument TD1 protrudes from the opening portion 31a1 without the side face of the treatment instrument TD1 touching the surface of the ultrasound transducer section 33 including the ultrasound transducer 33a.

When the raising stand 51A is in a raised position as shown by a two-dot dashed line in FIG. 17, the protruding direction of the treatment instrument TD1 is changed by the raising stand 51A.

After the distal end portion of the treatment instrument TD1 such as a cannula passes through the channel CH1 and comes out of the opening portion 31a1, if the raising lever 29 is raised, the raising stand 51A is raised as shown by a two-dot dashed line in FIG. 17, and the protruding direction of the distal end portion of the treatment instrument TD1 is changed. In FIG. 17, the raising stand 51A shown by a two-dot dashed line is raised to a maximum. The maximum raising angle of the treatment instrument TD1 is an angle $\theta 13$ with respect to the distal end direction of the insertion axis C0 of the distal end portion 21. The angle $\theta 13$ is defined by elasticity of the treatment instrument TD1 itself, the shape of the opening portion 31a1 and the shape of the distal end portion 51b of the raising stand 51A. In the case of FIG. 17, since the side face of the treatment instrument TD1 is in contact with a point P12 of the contact portion 51f1 of the distal end portion 51b of the raising stand 51A, the angle $\theta 13$ is substantially defined by the position of the treatment instrument TD1 in the opening portion 31a1 and the position of the point P12.

Figure 18:
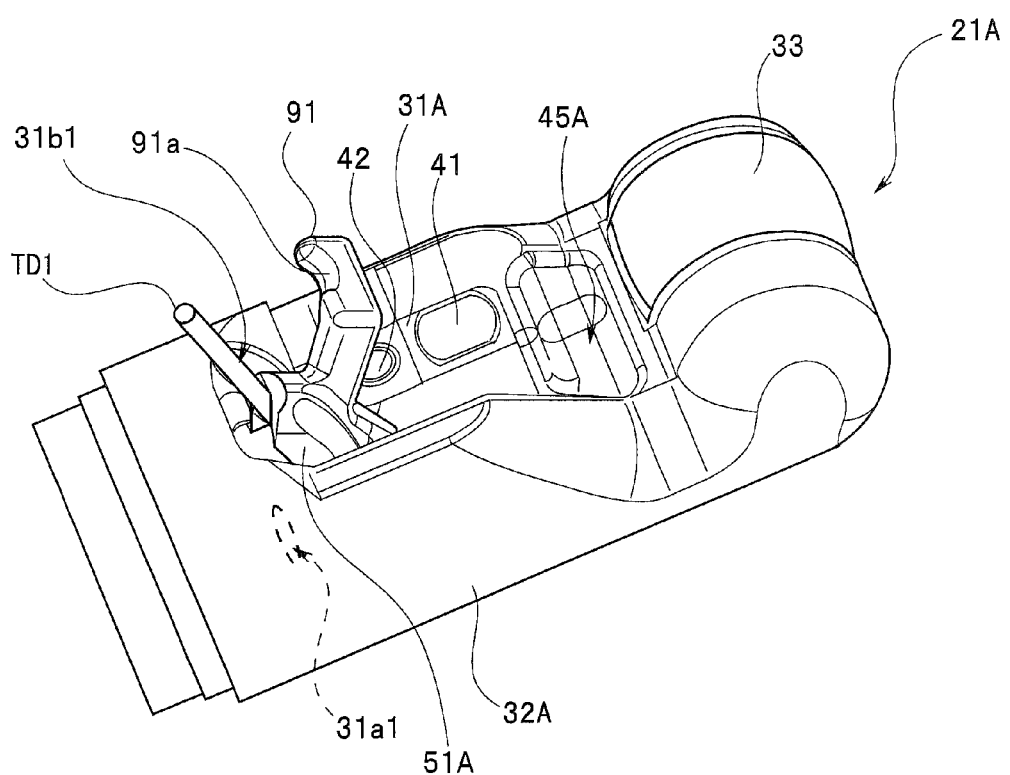
FIG. 18 is a perspective view of the distal end portion 21A illustrating the treatment instrument TD1 protruding when the raising stand 51A according to the second embodiment of the present invention is raised.

FIG. 18 is a perspective view of the distal end portion 21A illustrating a protruding state of the treatment instrument TD1 when the raising stand 51A is raised.

Figure 19:
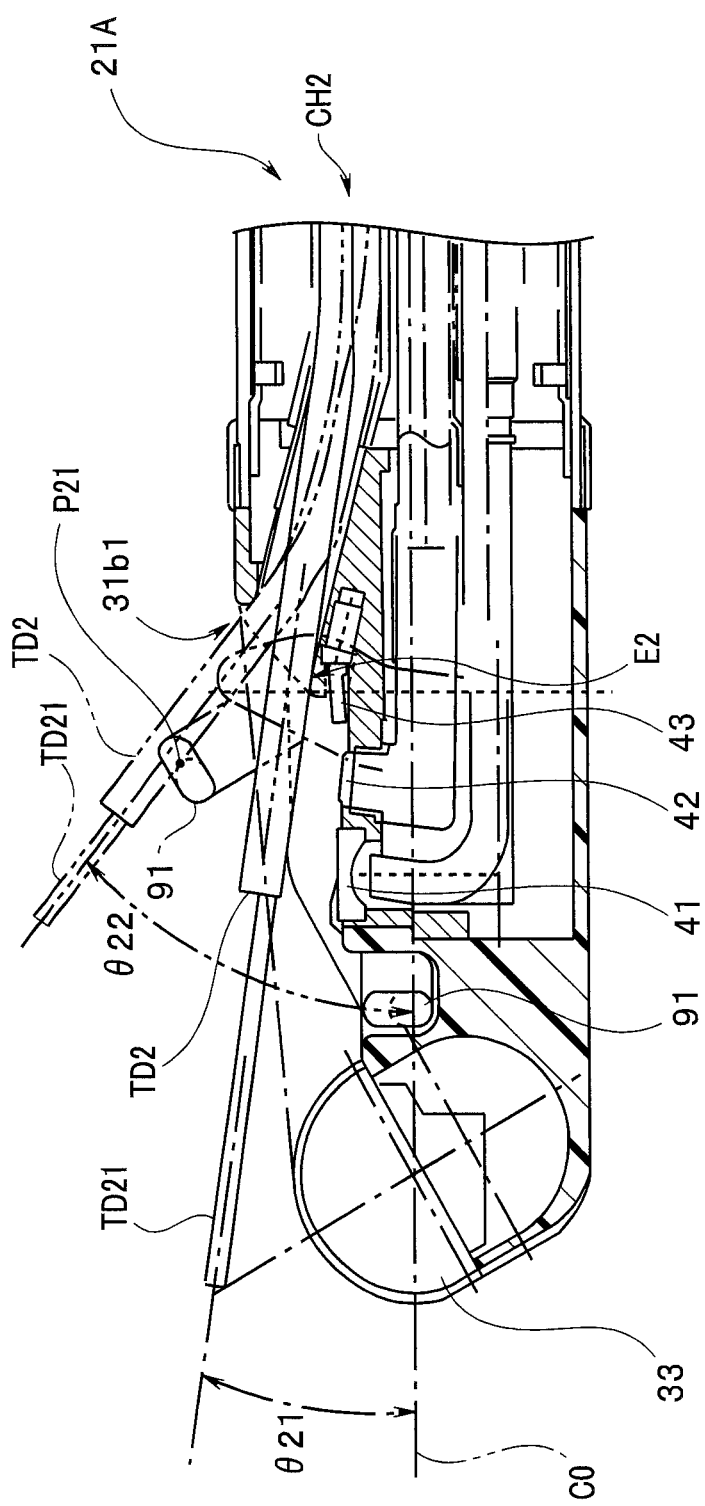
FIG. 19 is a cross-sectional view of the distal end portion 21A illustrating a treatment instrument TD2 protruding when the raising stand 51A according to the second embodiment of the present invention is raised and laid.

FIG. 19 is a cross-sectional view of the distal end portion 21A illustrating a protruding state of the treatment instrument TD2 when the raising stand 51A is raised and laid. FIG. 19 is a cross-sectional view along the straight line L11 in FIG. 14.

As shown by a solid line in FIG. 19, when the raising stand 51A is in a laid position, the side face of the treatment instrument TD2 protruding from the opening portion 31b1 of the channel CH2 comes into contact at the edge E2 of the opening portion 31b1 and protrudes from the opening portion 44A.

When the raising stand 51A is in a laid position, if the distal end portion of the treatment instrument TD2 passes through the channel CH2 and protrudes from the opening portion 31b1, the treatment instrument TD2 protrudes from the opening portion 44A with the side face of the treatment instrument TD2 sliding over the edge E2. The needle TD21 of the treatment instrument TD2 protrudes from the opening portion 44A at an angle $\theta 21$ with respect to the distal end direction of the insertion axis C0 of the distal end portion 21. The angle $\theta 21$ is defined by elasticity of the treatment instrument TD2 itself, the position and the shape of the edge E2 of the opening portion 31b1.

The treatment instrument TD2 does not touch the ultrasound transducer section 33 in this case, either. This prevents the treatment instrument TD2 from touching the ultrasound transducer section 33 and thereby damaging the ultrasound transducer section 33.

When the raising stand 51A is a raised condition as shown by a two-dot dashed line in FIG. 19, the protruding direction of the treatment instrument TD2 is changed by the extending portion 91 of the raising stand 51A.

After the distal end portion of the treatment instrument TD2 which is a puncture apparatus passes through the channel CH2 and comes out of the opening portion 31b1, if the raising lever 29 is raised, the raising stand 51A is raised as shown by a two-dot dashed line in FIG. 19, and the protruding direction of the distal end portion of the treatment instrument TD2 is changed by the extending portion 91 that extends from the raising stand 51A. The raising stand 51A shown by a two-dot dashed line in FIG. 19 is raised to a maximum. The maximum raising angle of the treatment instrument TD2 is an angle θ22 with respect to the distal end direction of the insertion axis C0 of the distal end portion 21. The angle θ22 is defined by elasticity of the treatment instrument TD2 itself, the shape of the opening portion 31b1 and the position and the shape of the contact portion 91a of the extending portion 91. In the case of FIG. 19, since the side face of the treatment instrument TD2 is in contact with a point P21 of the contact portion 91a of the extending portion 91, the angle θ22 is substantially defined by the position of the treatment instrument TD2 and the position of the point P21 in the opening portion 31b1.

Figure 20:
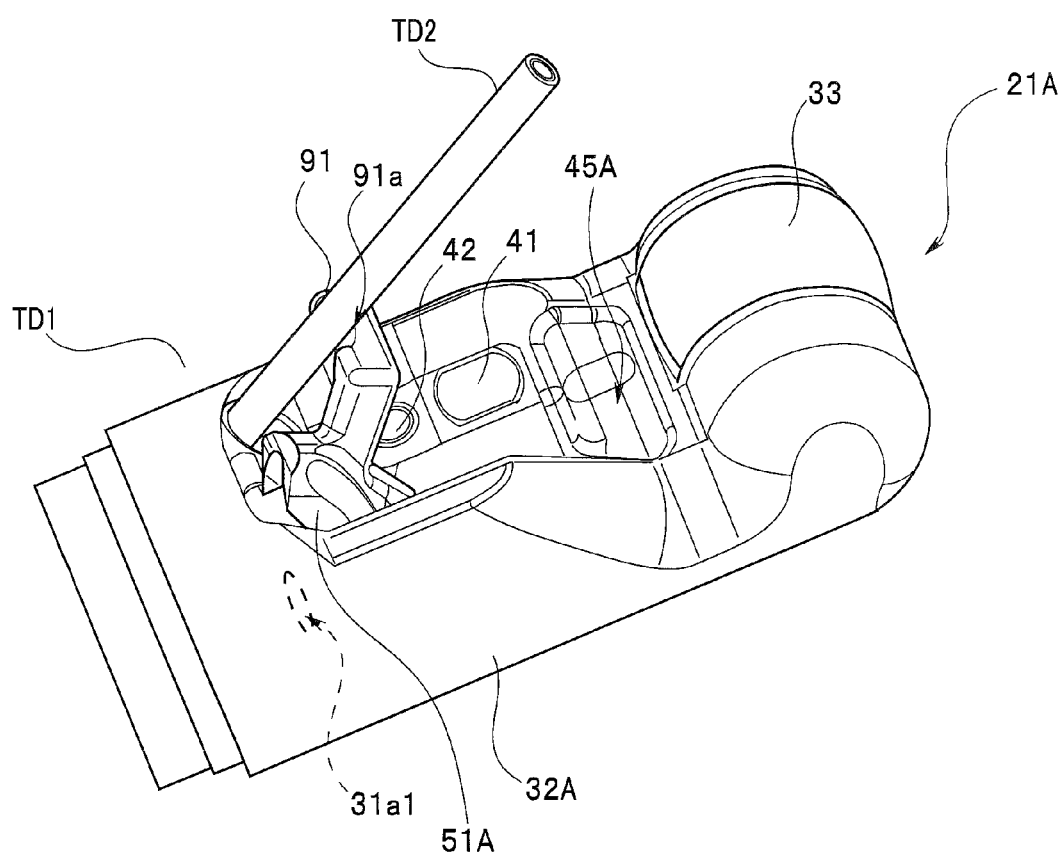
FIG. 20 is a perspective view of the distal end portion 21A illustrating the treatment instrument TD2 protruding when the raising stand 51A according to the second embodiment of the present invention is raised.

FIG. 20 is a perspective view of the distal end portion 21A illustrating a protruding state of the treatment instrument TD2 when the raising stand 51A is raised.

As described above, when the raising stand 51A is in a raised position and the treatment instrument TD1 protrudes from the opening portion 31a1, the contact portion 51f is provided on the raising stand 51A so that the side face of the treatment instrument TD1 comes into contact with the contact portion 51f.

Furthermore, when the raising stand 51A is in a raised position and the treatment instrument TD2 protrudes from the opening portion 31b1, the contact portion 91a is provided on the raising stand 51A so that the side face of the treatment instrument TD2 comes into contact with the contact portion 91a of the extending portion 91.

The contact portion 51f and the contact portion 91a are located respectively apart in a direction orthogonal to the insertion axis C0 at the end portion of the raising stand 51A.

The angle θ13 is 90 degrees or more and 130 degrees or less, and preferably 100 to 110 degrees. The angle θ22 is 10 degrees or more and 40 degrees or less, and preferably from 30 to 35 degrees.

As described above, according to the present embodiment, it is possible to perform both endoscopic retrograde cholangiopancreatography (ERCP) and endoscopic ultrasound-guided fine needle aspiration (EUS-FNA) using one ultrasound endoscope without increasing the length of the distal end rigid portion of the insertion portion.

According to the present invention, it is possible to perform both endoscopic retrograde cholangiopancreatography (ERCP) and endoscopic ultrasound-guided fine needle aspiration (EUS-FNA) using one ultrasound endoscope, thereby alleviate the burden on a patient, shorten the operation time without forcing the operator to perform complicated manipulation, further reduce introduction costs in a hospital, reduce the number of times for performing cleaning disinfecting or the like, and thereby implement an ultrasound endoscope with easy hygiene management.

What is claimed is:

1. An ultrasound endoscope comprising:
   an insertion portion configured to extend in a longitudinal direction and be inserted into a living body;
   an ultrasound transducer provided at a distal end portion of the insertion portion and configured to emit ultrasound sideward at a predetermined angle with respect to an insertion axis of the insertion portion;
   a distal end rigid portion provided at the distal end portion of the insertion portion and having a concave portion;
   a first opening portion provided at the distal end portion of the insertion portion, the first opening portion being provided at the concave portion;
   a second opening portion provided at the distal end portion of the insertion portion, the second opening portion being located at a position in a vicinity of an opening of the concave portion on an upper side with respect to the first opening portion in a direction toward the opening of the concave portion from a bottom surface of the concave portion; and
   a raising stand provided at the distal end portion of the insertion portion, wherein the raising stand is configured to be movable between a first position proximate to the first opening portion and the second opening portion and a second position away from the first opening portion and the second opening portion,
   wherein the raising stand comprises:
      a first contact portion provided along the raising stand from a proximal end portion of the raising stand to a distal end portion of the raising stand and that comes into contact with a side face of a first treatment instrument protruding from the first opening portion to cause the first treatment instrument to extend in a first direction; and
      a second contact portion provided on the distal end portion of the raising stand and that comes into contact with a side face of a second treatment instrument protruding from the second opening portion to cause the second treatment instrument to extend in a second direction different from the first direction.

2. The ultrasound endoscope according to claim 1,
   wherein the concave portion is formed in one side face of the distal end portion of the insertion portion, the concave portion being configured to accommodate the raising stand, and
   wherein the first opening portion is disposed in the concave portion.

3. The ultrasound endoscope according to claim 2, wherein the first opening portion and the second opening portion are arranged side by side along the direction from the bottom surface of the concave portion toward the opening of the concave portion when the insertion portion is seen from a distal end side of the insertion portion.

4. The ultrasound endoscope according to claim 2, wherein the first opening portion and the second opening portion are arranged along a direction having a predetermined angle with respect to the direction from the bottom surface of the concave portion toward the opening of the concave portion when the insertion portion is seen from a distal end side of the insertion portion.

5. The ultrasound endoscope according to claim 4,
   wherein when the raising stand is located at the first position and the first treatment instrument protrudes from the first opening portion, the first contact portion is provided on the raising stand so that a side face of the first treatment instrument comes into contact with the first contact portion,
   wherein when the raising stand is located at the first position and the second treatment instrument protrudes from the second opening portion, the second contact portion is provided on the raising stand so that a side face of the second treatment instrument comes into contact with the second contact portion, and wherein the first contact portion and the second contact portion are respectively located apart in a direction orthogonal to the insertion axis at an end portion of the raising stand.

6. The ultrasound endoscope according to claim 1, wherein when the raising stand is located at the second position, the first treatment instrument protrudes from the first opening portion so that a side face of the first treatment instrument does not touch a surface of an ultrasound transducer section including the ultrasound transducer.

7. The ultrasound endoscope according to claim 1, wherein when the raising stand is located at the first position and the first treatment instrument protrudes from the first opening portion, the first treatment instrument protrudes at an angle of 90 degrees or more and 130 degrees or less with respect to a distal end direction of the insertion axis.

* * * * *